(12) United States Patent
Lee et al.

(10) Patent No.: US 7,041,618 B2
(45) Date of Patent: May 9, 2006

(54) SUPPORTED METALLOCENE CATALYST AND OLEFIN POLYMERIZATION USING THE SAME

(75) Inventors: Bun-Yeoul Lee, Taejeon (KR); Jae-Seung Oh, Taejeon (KR); Joo-Eun Lee, Taejeon (KR); Do-Hoon Lee, Yeosoo (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 10/666,618

(22) Filed: Sep. 18, 2003

(65) Prior Publication Data

US 2004/0058804 A1    Mar. 25, 2004

Related U.S. Application Data

(63) Continuation-in-part of application No. 09/526,035, filed on Mar. 15, 2000, now abandoned.

(30) Foreign Application Priority Data

Jun. 22, 1999    (KR) .................... 10-1999-0223575

(51) Int. Cl.
   *B01J 31/00*    (2006.01)
(52) U.S. Cl. ..................... 502/152; 502/155
(58) Field of Classification Search ............... 502/152, 502/155
   See application file for complete search history.

(56) References Cited

U.S. PATENT DOCUMENTS

| | | | |
|---|---|---|---|
| 5,006,500 A | 4/1991 | Chang | |
| 5,240,894 A | 8/1993 | Burkhardt et al. | |
| 5,324,800 A | 6/1994 | Welborn, Jr. et al. | |
| 5,466,766 A | 11/1995 | Patsidis et al. | |
| 5,739,225 A | 4/1998 | Tazaki et al. | |
| 5,767,209 A * | 6/1998 | McNally | 526/160 |
| 5,767,300 A | 6/1998 | Aulbach et al. | |
| 5,814,574 A * | 9/1998 | McNally | 502/103 |
| 5,910,566 A | 6/1999 | Ko et al. | |
| 6,117,811 A | 9/2000 | Gruter et al. | |
| 6,469,113 B1 * | 10/2002 | Lee et al. | 526/126 |
| 2003/0144135 A1 * | 7/2003 | Llinas et al. | 502/103 |

FOREIGN PATENT DOCUMENTS

| | | | |
|---|---|---|---|
| EP | 000293815 | * | 6/1988 |
| EP | 000839836 | * | 5/1998 |
| JP | 06-056928 | | 1/1994 |
| KR | 98-25282 | * | 7/1998 |

OTHER PUBLICATIONS

Lee et al., J. Organomet. Chem., vol. 552 (1998) pp. 313-317.*
Alexaleis, et al., Tetrahedron Lett., 2951 (1988).
Andresson, et al., Angew. Int. Ed. Engl. 15, 630 (1976).
Barklay, et al., Chemistry and Industry (London), 1710 (1964).
Blü mel. J. Am. Chem. Soc., 117, 2112 (1995).
Bongini, et al., A Simple and Practical Method for Tetrahydropyranylation of Alcohols and Phenols, Synthesis, 618 (1979).
Dubois, et al., J. Am. Chem. Soc. 115, 1190 (1993).
Soga, Makromol. Chem., Rapid Commun., 13, 221 (1992).
Soga, Makromol. Chem., Rapid Commun., 15, 139 (1994).

* cited by examiner

Primary Examiner—J. A. Lorengo
Assistant Examiner—J. Pasterczyk
(74) Attorney, Agent, or Firm—McKenna Long & Aldridge LLP

(57) ABSTRACT

The present invention relates to a metallocene compound having a functional group that facilitates the preparation of the supported metallocene catalyst for olefin polymerization and the olefin polymerization process using the same. The metallocene compounds in this invention are strongly supported on the inorganic support due to the strong chemical bond of the ligand of the metallocene compound with the silica surface, which leads to minimize leaching of the catalyst during the activation process. Therefore, the supported catalyst of this invention allows the olefin polymerization process to proceed without any fouling in the reactor with a slurry or a gas phase process, and the morphology and bulk density of the polymer produced are much better defined than those produced by conventional methods.

11 Claims, 2 Drawing Sheets

SUPPORTED METALLOCENE CATALYST AND OLEFIN POLYMERIZATION USING THE SAME

RELATED APPLICATIONS

This application is a continuation-in-part of U.S. application Ser. No. 09/526,035, filed Mar. 15, 2000, now abandoned.

FIELD OF THE INVENTION

The present invention relates to a metallocene compound having a functional group that facilitates the preparation of a supported metallocene catalyst for olefin polymerization and a method of olefin polymerization using the same.

BACKGROUND OF THE INVENTION

In 1976, Professor Kaminsky of Germany reported that olefin polymerization could be accomplished using a zirconocene dichloride compound as a catalyst with methylaluminoxane (MAO), which was obtained through partial hydrolysis of trimethylaluminum, as a co-catalyst. See A. Anderson, et al., *Angew. Chem., Int. Ed. Engl.* 15, 630 (1976). Thereafter, Exxon showed that the activity of a catalyst and the molecular weight of the resulting polymer could be controlled by changing the substituents on the cyclopentadienyl ligand, and secured a patent (U.S. Pat. No. 5,324,800) on olefin polymerization utilizing the specified metallocene compounds with various substituent groups.

A homogeneous metallocene catalyst exhibits unique polymerization characteristics which cannot be obtained by conventional Ziegler-Natta catalysts. That is, the molecular weight distribution of the resulting polymer is narrow, co-polymerization is easy, and the co-monomer distribution is uniform. In the case of propylene polymerization, the tacticity of polymer can be controlled via the molecular symmetry of catalyst. These unique characteristics not only opened up a way to produce new polymers which are not attainable by conventional Ziegler-Natta catalysts, but also provided a way to make tailor-made polymers. Accordingly, there has been continuous interest in this catalyst system.

In a gas phase or a slurry process, particle morphology and the bulk density of the polymer are preferably controlled to increase the mobility of polymer and the production rate per reactor unit volume. Also, reactor fouling, a phenomenon wherein polymer sticks to the reactor wall and agitator blades, is preferably avoided for a continuous operation. To solve these problems, the catalyst is preferably anchored on a suitable support.

The following are conventional preparation methods for supported metallocene catalysts: 1) a metallocene compound is adsorbed on a support, and then activated by treatment with aluminoxane (W. Kaminsky, *Makromol. Chem., Rapid Commun.* 14, 239 (1993); 2) aluminoxane is supported first, and then a metallocene compound is supported (K. Soga, *Makromol. Chem. Rapid Commun.* 13, 221 (1992); U.S. Pat. No. 5,006,500; U.S. Pat. No. 5,086,025); 3) a metallocene compound is treated with aluminoxane, and then adsorbed on a support (U.S. Pat. No. 5,240,894); and 4) the anchoring of catalyst is achieved by a chemical reaction between the ligand of a metallocene compound and a support.

In one method, the metal is ligated after the ligand is supported. (K. Soga, H. J. Kim, T. Shiono, *Makromol., Rapid Commun.* 15, 139 (1994), Japanese Laid-open Patent No. Heisei 6-56928, U.S. Pat. No. 5,466,766). In the other methods, a metallocene compound with suitable ligands is prepared and then it is supported on a support by chemical reaction. The suitable ligands in this case usually contain silicon based functional groups such as alkoxysilane or halosilane (European Patent No. 293815, U.S. Pat. No. 5,202,398, U.S. Pat. No. 5,767,300, European Patent No. 839836, Korean Patent Application Nos. 98-12660 and 99-06955). However, metallocene compounds with silicon containing functional group are not easy to make and do not have good stabilities. For example, European Patent No. 839836 discloses a metallocene compound having the functional group —$OSiMe_3$. The yield in the metallation step, which is the last step in the synthesis, is only around 28 to 51% which is a disadvantage in commercial applications.

U.S. Pat. No. 5,814,574 discloses a supported polymerization catalyst which is prepared by the binding of an inorganic support with a metallocene compound containing a functional group selected from alkoxyalkyl, heterocycle oxygen group, and alkyl heterocycle oxygen group. U.S. Pat. No. 5,767,209 discloses the polymerization of olefins at a specified temperature and pressure utilizing a supported catalyst. In this patent, the metallocene compound with Lewis base functionalities, such as oxygen, silicon, phosphorus, nitrogen or sulfur atoms, is bound to an inorganic support in the absence of aluminoxane to give a supported catalyst. However, the catalyst bound to and supported on the inorganic support surface by the Lewis acid-base reaction leaches out of the surface upon activation with a Lewis acidic aluminoxane co-catalyst. The leaching of the catalyst results in reactor fouling and irregular morphology, which are detrimental in a slurry or a gas phase process.

Metallocene catalysts with suitable functional groups can be supported on a silica surface by the reaction of an alkoxysilane or halosilane functional group with a surface hydroxyl group or highly reactive siloxane group, which is formed from the dehydroxylation of the silica above 600° C., as shown in Reaction Formulas 1 through 3.

Reaction Formula 1

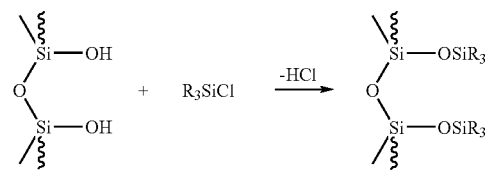

Reaction Formula 2

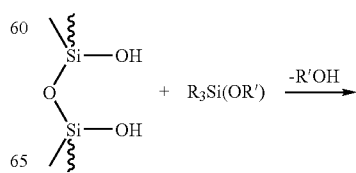

-continued

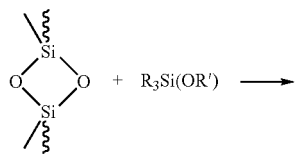

Reaction Formula 2

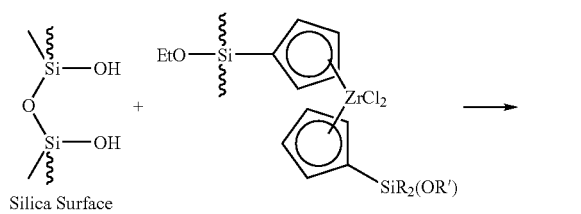

EP 293815 A1 discloses a method in which a supported metallocene catalyst is prepared by the reaction of a metallocene compound containing a —C—SiR$_2$(OR') functional group (wherein R is a C$_{1-4}$ alkyl, C$_{6-10}$ aryl, or C$_{1-4}$ alkoxy, and OR' is a C$_{1-4}$ alkoxy) with a support hydroxyl group on its surface, as depicted in Reaction Formula 4.

Reaction Formula 4

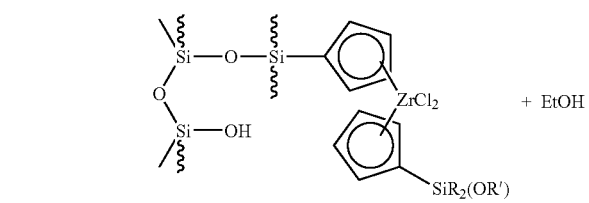 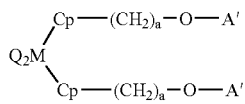

Silica Surface

In this reaction, a Si—OR' (silicon-based group) bond of the metallocene compound is reacted with a Si—OH group of the support material to produce a strongly bound, supported metallocene catalyst via Si—O—Si bond formation. However, an alkyl alcohol (R'OH) by-product is also formed during the reaction, and can act as a catalyst poison to lower activity of the resulting catalyst.

Reaction Formula 3 has been reported recently (*J. Am. Chem. Soc.* 117, 2112, (1995); *J. Am. Chem. Soc.* 115, 1190, (1993)) and is advantageous in the preparation of a supported metallocene catalyst because side reactions are minimized (Korean Patent Application No. 98-12660). As mentioned above, however, the catalyst with siloxane functional groups is not easy to make and has low stability. For example, catalysts containing an alkoxysilane group, [HMe$_2$Si—O—(CH$_2$)$_6$—C$_5$H$_4$]$_2$ZrCl$_2$ and [Me$_3$Si—O—(CH$_2$)$_6$—C$_5$H$_4$]$_2$ZrCl$_2$, were disclosed in the examples and comparative examples of Korean Patent Application No 99-06955. In the examples, the yield in the zirconation step, which is the last step of the synthesis, was below 60% and the catalysts were observed to degrade slowly over an extended period of time under an inert gas atmosphere at room temperature. Other catalysts are disclosed in *J. Organomet. Chem.* 552, 313, (1998).

SUMMARY OF THE INVENTION

It is an object of the present invention to provide a metallocene compound having a functional group that facilitates the preparation of the supported metallocene catalyst for olefin polymerization.

It is another object of the present invention to provide a supported metallocene catalyst using the above metallocene compound.

It is still another object of the present invention to provide a method for preparing a supported metallocene catalyst using the above metallocene compound.

It is still another object of the present invention to provide a process for preparing olefin polymer using the supported metallocene catalyst.

In a first embodiment, a metallocene compound is provided, the metallocene compound comprising Chemical Formula 7:

$$Q_2M\begin{matrix}Cp-(CH_2)_a-O-A'\\Cp-(CH_2)_a-O-A'\end{matrix}$$

wherein M comprises a transition metal of Group 4; Cp, which can be the same or different, comprises a cyclopentadienyl ring, wherein the cyclopentadienyl ring is unsubstituted or substituted by a moiety selected from the group consisting of alkyl, cycloalkyl, aryl, alkenyl, alkylaryl, arylalkyl, and arylalkenyl; Q, which can be the same or different, comprises halogen or a moiety comprising from 1 to 20 carbon atoms, wherein the moiety is selected from the group consisting of alkyl, alkenyl, aryl, alkylaryl, arylalkyl, and alkylidene, wherein the alkyl, alkenyl, aryl, alkylaryl, arylalkyl, and alkylidene; A', which can be the same or different, is selected from the group consisting of methoxymethyl, t-butoxymethyl, tetrahydropyranyl, tetrahydrofuranyl, 1-ethoxylethyl, 1-methyl-1-methoxyethyl, and t-butyl; and a comprises an integer of from 4 to 8.

In an aspect of the first embodiment, A' comprises t-butyl.

In an aspect of the first embodiment, a is 6.

In a second embodiment, a supported metallocene catalyst is provided, the supported metallocene catalyst represented by formula:

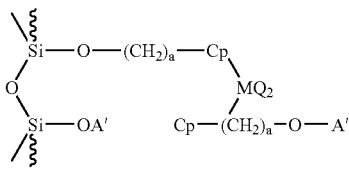

wherein M comprises a transition metal of Group 4; Cp, which can be the same or different, comprises a cyclopentadienyl ring, wherein the cyclopentadienyl ring is unsubstituted or substituted by a moiety selected from the group consisting of alkyl, cycloalkyl, aryl, alkenyl, alkylaryl, arylalkyl, and arylalkenyl; Q, which can be the same or different, comprises halogen or a moiety comprising from 1 to 20 carbon atoms, wherein the moiety is selected from the group consisting of alkyl, alkenyl, aryl, alkylaryl, arylalkyl, and alkylidene, wherein the alkyl, alkenyl, aryl, alkylaryl, arylalkyl, and alkylidene; A', which can be the same or different, is selected from the group consisting of methoxymethyl, t-butoxymethyl, tetrahydropyranyl, tetrahydrofuranyl, 1-ethoxyethyl, 1-methyl-1-methoxyethyl, and t-butyl; and a comprises an integer of from 4 to 8.

In an aspect of the second embodiment, A' comprises t-butyl.

In an aspect of the second embodiment, a is 6.

In a third embodiment, a method for preparing a supported metallocene catalyst is provided, the method comprising the step of reacting a metallocene compound of Chemical Formula 7:

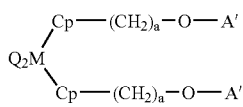

with a silica support of formula:

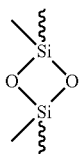

in an organic solvent, wherein: M comprises a transition metal of Group 4; Cp, which can be the same or different, comprises a cyclopentadienyl ring, wherein the cyclopentadienyl ring is unsubstituted or substituted by a moiety selected from the group consisting of alkyl, cycloalkyl, aryl, alkenyl, alkylaryl, arylalkyl, and arylalkenyl; Q, which can be the same or different, comprises halogen or a moiety comprising from 1 to 20 carbon atoms, wherein the moiety is selected from the group consisting of alkyl, alkenyl, aryl, alkylaryl, arylalkyl, and alkylidene, wherein the alkyl, alkenyl, aryl, alkylaryl, arylalkyl, and alkylidene; A', which can be the same or different, is selected from the group consisting of methoxymethyl, t-butoxymethyl, tetrahydropyranyl, tetrahydrofuranyl, 1-ethoxyethyl, 1-methyl-1-methoxyethyl, and t-butyl; and a comprises an integer of from 4 to 8; whereby one O-A' bond in the metallocene compound of Chemical Formula 7 is cleaved and two new bonds are formed, wherein the metallocene compound is bonded to a silica atom of the silica support via an oxygen atom, and simultaneously A' is bonded to another silica atom of the silica support via an oxygen atom, to yield a supported metallocene catalyst of formula:

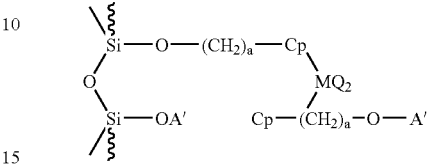

whereby one of the O-A' bonds in the Chemical Formula 1 is cleaved so that the metallocene compound is bonded to a silica atom of the silica support via an oxygen atom, and simultaneously A' is bonded to another silica atom of the silica support via an oxygen atom, as depicted in Reaction Formula 5.

Reaction Formula 5

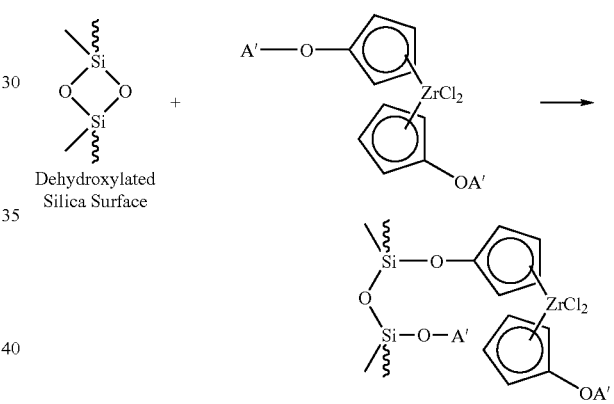

In an aspect of the third embodiment, the silica support comprises a hydroxyl group amount of less than 0.5 mmol/g.

In an aspect of the third embodiment, A' comprises t-butyl.

In an aspect of the third embodiment, a is 6.

In a fourth embodiment, a process for olefin polymerization is provided which comprises conducting the polymerization in the presence of the catalyst system comprising a supported metallocene catalyst represented by the formula:

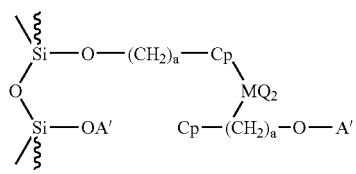

and one or more co-catalysts selected from the compounds described by the following Chemical Formulae 8, 9, 10, or 11 wherein Chemical Formulae 8 and 9 are respectively:

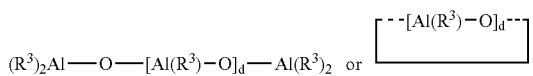

wherein each $R^3$, which can be the same or different, is a halogen atom, a hydrocarbyl group having from 1 to 40 carbon atoms, or a halogen substituted hydrocarbyl group having from 1 to 40 carbon atoms; and d is an integral number greater than 2; wherein Chemical Formula 10 is:

wherein each $R^4$, which can be the same as or different, is a halogen atom, a hydrocarbyl group having from 1 to 40 carbon atoms, or a halogen substituted hydrocarbyl group having from 1 to 40 carbon atoms); and wherein Chemical Formula 11 is:

wherein, $[L]^+$ is a cation composed of an inorganic or organic group; N is an element of Group 13 (IVB in the previous IUPAC form); and each E, which can be the same as or different from other E, is an aryl group having from 6 to 40 carbon atoms, where at least one of the hydrogen atoms of the aryl group is substituted with a halogen atom, a hydrocarbyl group having from 1 to 40 carbon atoms, an alkoxy group, a phenoxy group, or a hydrocarbyl group having from 1 to 40 carbon atoms with nitrogen, phosphorus, sulfur, or oxygen atom.

In a fifth embodiment, a metallocene compound is provided that is represented by Chemical Formula 1 or Chemical Formula 2, wherein Chemical Formula 1 comprises:

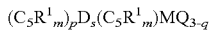

and wherein Chemical Formula 2 comprises:

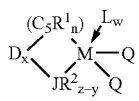

wherein at least one hydrogen atom of $R^1$, $R^2$, and D is substituted by a group of Chemical Formula 6, wherein: M is a transition metal of Group 4; $(C_5R^1_m)$ and $(C_5R^1_n)$ each comprise a cyclopentadienyl ring, wherein each $R^1$, which can be the same or different, is selected from the group consisting of hydrogen, $C_{1-40}$ alkyl, $C_{1-40}$ cycloalkyl, $C_{1-40}$ aryl, $C_{1-40}$ alkenyl, $C_{1-40}$ alkylaryl, $C_{1-40}$ arylalkyl, $C_{1-40}$ arylalkenyl, and a metalloid of Group 14 substituted by a hydrocarbyl group; and two $R^1$ can form a hydrocarbyl group which joins together two adjacent carbon atoms of a cyclopentadienyl ring to form one or more $C_4$–$C_{16}$ rings; D is selected from the group consisting of an alkylene carbon chain, an arylene carbon chain, an alkenylene carbon chain, a dialkyl germanium, a dialkyl silicon, an alkyl phospine, an alkyl amine group substituting on and bridging two cyclopentadienyl ligands, and an alkyl amine group substituting on and bridging a cyclopentadienyl ligand and $JR^2_{z-y}$ ligand by a covalent bond; $R^2$ is selected from the group consisting of hydrogen, $C_{1-40}$ alkyl, $C_{1-40}$ aryl, $C_{1-40}$ alkenyl, $C_{1-40}$ alkylaryl, and $C_{1-40}$ arylalkyl; J comprises an element of Group 15 or Group 16; each Q, which can be the same or different, is selected from the group consisting of halogen, $C_{1-20}$ alkyl, $C_{1-20}$ alkenyl, $C_{1-20}$ aryl, $C_{1-20}$ alkylaryl, and $C_{1-20}$ alkylidene; L comprises a Lewis base; s is 0 or 1 and p is 0, 1 or 2, provided that when p is 0 then s is 0, when s is 1 then m is 4 and p is 1, and when s is 0 then m is 5 and p is 0; z is a valence number of J, provided that when J is an atom of Group 15 then z is 3, and when J is an atom of Group 16 then z is 2; x is 0 or 1, provided that when x is 0 then n is 5, y is 1, and w is greater than 0, and when x is 1, then n is 4, y is 2, and w is 0; and wherein Chemical Formula 6 comprises:

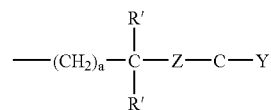

wherein, Z is oxygen atom or sulfur atom; each R', which can be the same or different, is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, and $C_{1-20}$ arylalkenyl; and two R' can join together to form a ring; Y is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, $C_{1-20}$ arylalkenyl, $C_{1-20}$ alkoxy, $C_{1-20}$ aryloxy, $C_{1-20}$ alkylthio, $C_{1-20}$ arylthio, phenyl, and substituted phenyl; and Y and R' can join together to form a ring; a is an integer of 4 to 8, provided that when Z is a sulfur atom then Y is alkoxy or aryloxy; and when Y is not an alkoxy or aryloxy then Z is an oxygen atom.

In a sixth embodiment, a supported metallocene catalyst is provided that is prepared by the reaction of a metallocene compound of Chemical Formula 1 or Chemical Formula 2 with a silica support in an organic solvent, wherein Chemical Formula 1 comprises:

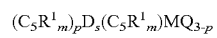

and wherein Chemical Formula 2 comprises:

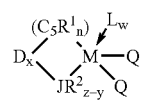

wherein at least one hydrogen atom of $R^1$, $R^2$, and D is substituted by a group of Chemical Formula 6, wherein: M is a transition metal of Group 4; $(C_5R^1_m)$ and $(C_5R^1_n)$ each comprise a cyclopentadienyl ring, wherein each $R^1$, which can be the same or different, is selected from the group consisting of hydrogen, $C_{1-40}$ alkyl, $C_{1-40}$ cycloalkyl, $C_{1-40}$ aryl, $C_{1-40}$ alkenyl, $C_{1-40}$ alkylaryl, $C_{1-40}$ arylalkyl, $C_{1-40}$ arylalkenyl, and a metalloid of Group 14 substituted by a hydrocarbyl group; and two $R^1$ can form a hydrocarbyl group which joins together two adjacent carbon atoms of a cyclopentadienyl ring to form one or more $C_4$–$C_{16}$ rings; D is selected from the group consisting of an alkylene carbon chain, an arylene carbon chain, an alkenylene carbon chain, a dialkyl germanium, a dialkyl silicon, an alkyl phosphine, an alkyl amine group substituting on and bridging two cyclopentadienyl ligands, and an alkyl amine group substi tuting on and bridging a cyclopentadienyl ligand and $JR^2_{z-y}$ ligand by a covalent bond; $R^2$ is selected from the group consisting of hydrogen, $C_{1-40}$ alkyl, $C_{1-40}$ aryl, $C_{1-40}$ alkenyl, $C_{1-40}$ alkylaryl, and $C_{1-40}$ arylalkyl; J comprises an element of Group 15 or Group 16; each Q, which can be the same or different, is selected from the group consisting of halogen, $C_{1-20}$ alkyl, $C_{1-20}$ alkenyl, $C_{1-20}$ aryl, $C_{1-20}$ alkylaryl, and $C_{1-20}$ alkylidene; L comprises a Lewis base; s is 0 or 1 and p is 0, 1 or 2, provided that when p is 0 then s is 0, when s is 1 then m is 4, and when s is 0 then m is 5; z is a valence number of J, provided that when J is an atom of Group 15 then z is 3, and when J is an atom of Group 16 then z is 2; x is 0 or 1, provided that when x is 0 then n is 5, y is 1, and w is greater than 0, and when x is 1, then n is 4, y is 2, and w is 0; and wherein Chemical Formula 6 comprises:

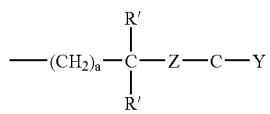

wherein, Z is oxygen atom or sulfur atom; each R', which can be the same or different, is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, and $C_{1-20}$ arylalkenyl; and two R' can join together to form a ring; Y is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, $C_{1-20}$ arylalkenyl, $C_{1-20}$ alkoxy, $C_{1-20}$ aryloxy, $C_{1-20}$ alkylthio, $C_{1-20}$ arylthio, phenyl, and substituted phenyl; and Y and R' can join together to form a ring; a is an integer of 4 to 8, provided that when Z is a sulfur atom then Y is alkoxy or aryloxy; and when Y is not an alkoxy or aryloxy then Z is an oxygen atom; and wherein the silica support is of formula:

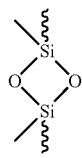

whereby an oxygen-carbon bond in Chemical Formula 6 of the metallocene compound is cleaved to yield a metallocene compound portion and a remaining portion, and whereby the metallocene compound portion is bonded to a silica atom of the silica support via an oxygen atom, and simultaneously the remaining portion is bonded to another silica atom of the silica support via an oxygen atom.

In a seventh embodiment, a supported metallocene catalyst is provided that is prepared by the reaction of a metallocene compound of Chemical Formula 1 or Chemical Formula 2 with a silica support, wherein Chemical Formula 1 comprises:

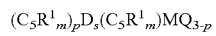

and wherein Chemical Formula 2 comprises:

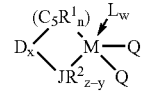

wherein at least one hydrogen atom of $R^1$, $R^2$, and D is substituted by a group of Chemical Formula 6, wherein: M is a transition metal of Group 4; $(C_5R^1_m)$ and $(C_5R^1_n)$ each comprise a cyclopentadienyl ring, wherein each $R^1$, which can be the same or different, is selected from the group consisting of hydrogen, $C_{1-40}$ alkyl, $C_{1-40}$ cycloalkyl, $C_{1-40}$ aryl, $C_{1-40}$ alkenyl, $C_{1-40}$ alkylaryl, $C_{1-40}$ arylalkyl, $C_{1-40}$ arylalkenyl, and a metalloid of Group 14 substituted by a hydrocarbyl group; and two $R^1$ can form a hydrocarbyl group which joins together two adjacent carbon atoms of a cyclopentadienyl ring to form one or more $C_4$–$C_{16}$ rings; D is selected from the group consisting of an alkylene carbon chain, an arylene carbon chain, an alkenylene carbon chain, a dialkyl germanium, a dialkyl silicon, an alkyl phosphine, an alkyl amine group substituting on and bridging two cyclopentadienyl ligands, and an alkyl amine group substituting on and bridging a cyclopentadienyl ligand and $JR^2_{z-y}$ ligand by a covalent bond; $R^2$ is selected from the group consisting of hydrogen, $C_{1-40}$ alkyl, $C_{1-40}$ aryl, $C_{1-40}$ alkenyl, $C_{1-40}$ alkylaryl, and $C_{1-40}$ arylalkyl; J comprises an element of Group 15 or Group 16; each Q, which can be the same or different, is selected from the group consisting of halogen, $C_{1-20}$ alkyl, $C_{1-20}$ alkenyl, $C_{1-20}$ aryl, $C_{1-20}$ alkylaryl, and $C_{1-20}$ alkylidene; L comprises a Lewis base; s is 0 or 1 and p is 0, 1 or 2, provided that when p is 0 then s is 0, when s is 1 then m is 4, and when s is 0 then m is 5; z is a valence number of J, provided that when J is an atom of Group 15 then z is 3, and when J is an atom of Group 16 then z is 2; x is 0 or 1, provided that when x is 0 then n is 5, y is 1, and w is greater than 0, and when x is 1, then n is 4, y is 2, and w is 0; and wherein Chemical Formula 6 comprises:

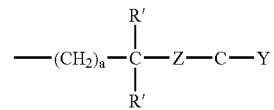

wherein, Z is oxygen atom or sulfur atom; each R', which can be the same or different, is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, and $C_{1-20}$ arylalkenyl; and two R' can join together to form a ring; Y is selected from the group consisting of hydrogen, $C_{1-40}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, $C_{1-20}$ arylalkenyl, $C_{1-20}$ alkoxy, $C_{1-20}$ aryloxy, $C_{1-20}$ alkylthio, $C_{1-20}$ arylthio, phenyl, and substituted phenyl; and Y and R' can join together to form a ring; a is an integer of 4 to 8, provided that when Z is a sulfur atom then Y is alkoxy or aryloxy; and when Y is not an alkoxy or aryloxy then Z is an oxygen atom; and wherein the silica support is of formula:

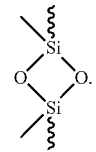

In an eighth embodiment, a process for olefin polymerization is provided which comprises conducting the polymerization in the presence of the catalyst system comprising a supported metallocene catalyst prepared by the reaction of reaction of a metallocene compound of Chemical Formula 1 or Chemical Formula 2 with a silica support and at least one co-catalyst, wherein Chemical Formula 1 comprises:

$(C_5R^1_m)_p D_s(C_5R^1_m)MQ_{3-p}$ and wherein Chemical Formula 2 comprises:

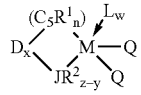

wherein at least one hydrogen atom of $R^1$, $R^2$, and D is substituted by a group of Chemical Formula 6, wherein: M is a transition metal of Group 4; $(C_5R^1_m)$ and $(C_5R^1_n)$ each comprise a cyclopentadienyl ring, wherein each $R^1$, which can be the same or different, is selected from the group consisting of hydrogen, $C_{1-40}$ alkyl, $C_{1-40}$ cycloalkyl, $C_{1-40}$ aryl, $C_{1-40}$ alkenyl, $C_{1-40}$ alkylaryl, $C_{1-40}$ arylalkyl, $C_{1-40}$ arylalkenyl, and a metalloid of Group 14 substituted by a hydrocarbyl group; and two $R^1$ can form a hydrocarbyl group which joins together two adjacent carbon atoms of a cyclopentadienyl ring to form one or more $C_4$-$C_{16}$ rings; D is selected from the group consisting of an alkylene carbon chain, an arylene carbon chain, an alkenylene carbon chain, a dialkyl germanium, a dialkyl silicon, an alkyl phosphine, an alkyl amine group substituting on and bridging two cyclopentadienyl ligands, and an alkyl amine group substituting on and bridging a cyclopentadienyl ligand and $JR^2_{z-y}$ ligand by a covalent bond; $R^2$ is selected from the group consisting of hydrogen, $C_{1-40}$ alkyl, $C_{1-40}$ aryl, $C_{1-40}$ alkenyl, $C_{1-40}$ alkylaryl, and $C_{1-40}$ arylalkyl; J comprises an element of Group 15 or Group 16; each Q, which can be the same or different, is selected from the group consisting of halogen, $C_{1-20}$ alkyl, $C_{1-20}$ alkenyl, $C_{1-20}$ aryl, $C_{1-20}$ alkylaryl, and $C_{1-20}$ alkylidene; L comprises a Lewis base; s is 0 or 1 and p is 0, 1 or 2, provided that when p is 0 then s is 0, when s is 1 then m is 4, and when s is 0 then m is 5; z is a valence number of J, provided that when J is an atom of Group 15 then z is 3, and when J is an atom of Group 16 then z is 2; x is 0 or 1, provided that when x is 0 then n is 5, y is 1, and w is greater than 0, and when x is 1, then n is 4, y is 2, and w is 0; and wherein Chemical Formula 6 comprises:

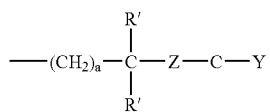

wherein, Z is oxygen atom or sulfur atom; each R', which can be the same or different, is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, and $C_{1-20}$ arylalkenyl; and two R' can join together to form a ring; Y is selected from the group consisting of hydrogen, $C_{1-20}$ alkyl, $C_{1-20}$ cycloalkyl, $C_{1-20}$ aryl, $C_{1-20}$ alkenyl, $C_{1-20}$ alkylaryl, $C_{1-20}$ arylalkyl, $C_{1-20}$ arylalkenyl, $C_{1-20}$ alkoxy, $C_{1-20}$ aryloxy, $C_{1-20}$ alkylthio, $C_{1-20}$ arylthio, phenyl, and substituted phenyl; and Y and R' can join together to form a ring;

a is an integer of 4 to 8, provided that when Z is a sulfur atom then Y is alkoxy or aryloxy; and when Y is not an alkoxy or aryloxy then Z is an oxygen atom; wherein the silica support is of formula:

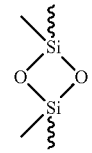

and wherein the co-catalyst is selected from the compounds described by the following Chemical Formulae 8, 9, 10, or 11 wherein Chemical Formulae 8 and 9 are respectively:

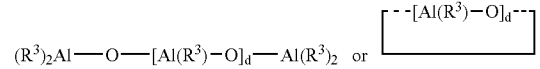

wherein each $R^3$, which can be the same or different, is a halogen atom, a hydrocarbyl group having from 1 to 40 carbon atoms, or a halogen substituted hydrocarbyl group having from 1 to 40 carbon atoms; and d is an integral number greater than 2; wherein Chemical Formula 10 is:

$Al(R^4)_3$ wherein each $R^4$, which can be the same as or different, is a halogen atom, a hydrocarbyl group having from 1 to 40 carbon atoms, or a halogen substituted hydrocarbyl group having from 1 to 40 carbon atoms); and wherein Chemical Formula 11 is:

$[L]^+[NE_4]^-$ wherein, $[L]^+$ is a cation composed of an inorganic or organic group; N is an element of Group 13 (IVB in the previous IUPAC form); and each E, which can be the same as or different from other E, is an aryl group having from 6 to 40 carbon atoms, where at least one of the hydrogen atoms of the aryl group is substituted with a halogen atom, a hydrocarbyl group having from 1 to 40 carbon atoms, an alkoxy group, a phenoxy group, or a hydrocarbyl group having from 1 to 40 carbon atoms with nitrogen, phosphorus, sulfur, or oxygen atom.

DETAILED DESCRIPTION OF THE PREFERRED EMBODIMENT

Figure 1:
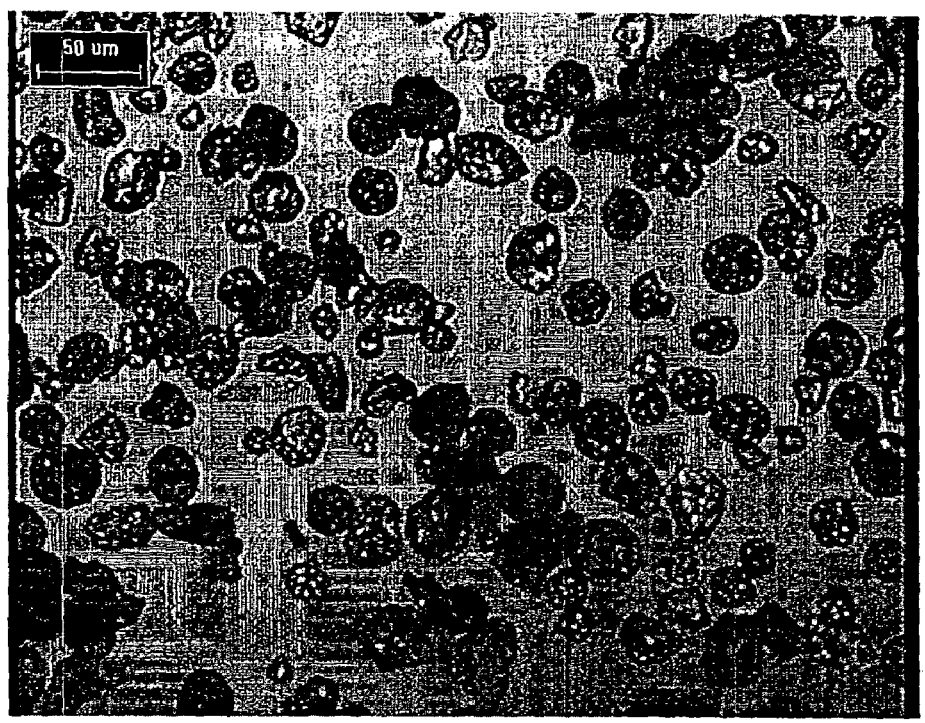
FIG. 1 is an optical microscope photograph of the supported catalyst morphology, wherein the supported catalyst was prepared by supporting the catalyst of Example 5 on a silica surface (100 times magnified)

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

A metallocene compound of a preferred embodiment which is useful in the preparation of a supported metallocene catalyst is represented by Chemical Formula 1 or Chemical Formula 2, in which at least one of the hydrogen atoms of $R^1$, $R^2$, or D is substituted by a group represented by Chemical Formula 3, Chemical Formula 4, or Chemical Formula 5.

Chemical Formula 1 is as follows:

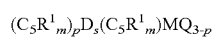

and Chemical Formula 2 is as follows:

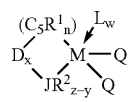

wherein M is a transition metal of Group 4 (IVA in the previous IUPAC form); $(C_5R^1_m)$ and $(C_5R^1_n)$ are independently selected from a cyclopentadienyl ligand, a substituted cyclopentadienyl ligand, or a substituted cyclopentadienyl ligand in which two adjacent carbon atoms of a $C_5$ are joined together to form one or more $C_4$–$C_{16}$ rings by a hydrocarbyl group, in which each $R^1$, which can be the same as or different from another other $R^1$, is a hydrogen atom, or an alkyl, cycloalkyl, aryl, alkenyl, alkylaryl, arylalkyl, or arylalkenyl group having from 1 to 40 carbon atoms, or a metalloid of Group 14 (IVB in the previous IUPAC form) substituted by a hydrocarbyl group; D is an alkylene carbon chain, arylene carbon chain, alkenylene carbon chain, dialkyl germanium, dialkyl silicon, alkyl phospine, or alkyl amine group substituting on and bridging two cyclopentadienyl ligands, or a cyclopentadienyl ligand and $JR^2_{z-y}$ ligands by a covalent bond; $R^2$ is a hydrogen atom, or an alkyl, aryl, alkenyl, alkylaryl, or arylalkyl group having from 1 to 40 carbon atoms; J is an element of Group 15 (VB in the previous IUPAC form) or Group 16 (VIB in the previous IUPAC form); each Q, which can be the same as or different from another Q, is a halogen atom, an alkyl, alkenyl, aryl, alkylaryl, or arylalkyl group having from 1 to 20 carbon atoms, or an alkylidene group from 1 to 20 carbon atoms; L is a Lewis base; s is 0 or 1 and p is 0, 1 or 2, provided that when p is 0 then s is 0, when s is 1 then m is 4 and p is 1, and when s is 0 then m is 5 and p is 0; z is a valence number of J, provided that when J is an atom of Group 15 (VB in the previous IUPAC form) then z is 3, and when J is an atom of Group 16 (VIB in the previous IUPAC form) then z is 2; x is 0 or 1, provided that when x is 0 then n is 5, y is 1, and w is greater than 0, and when x is 1 then n is 4, y is 2, and w is 0.

Chemical Formula 3 is as follows:

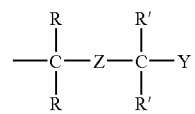

wherein Z is oxygen atom or sulfur atom; each R, which can be the same as or different from another R, is a hydrogen atom, an alkyl, cycloalkyl, aryl, alkenyl, alkylaryl, arylalkyl, or arylalkenyl group having from 1 to 20 carbon atoms; each R', which can be the same as or different from another R', is a hydrogen atom, an alkyl, cycloalkyl, aryl, alkenyl, alkylaryl, arylalkyl, or arylalkenyl group having from 1 to 20 carbon atoms, and two R' can join together to form a ring; Y is a hydrogen atom, an alkyl, cycloalkyl, aryl, alkenyl, alkylaryl, arylalkyl, or arylalkenyl, alkoxy, aryloxy, alkylthio, or arylthio group having from 1 to 20 carbon atoms, a phenyl, or a substituted phenyl, and Y and R' can join together to form a ring, provided that when Z is a sulfur atom, then Y is alkoxy or aryloxy.

Chemical Formula 4 is as follows:

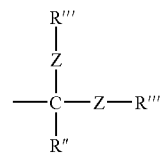

wherein Z is an oxygen atom or a sulfur atom and at least one Z is an oxygen atom; R" is a hydrogen atom, an alkyl, cycloalkyl, aryl, alkenyl, alkylaryl, arylalkyl, or arylalkenyl group having from 1 to 40 carbon atoms, and R" and R''' can join together to form a ring; each R''', which can be the same as or different from another R''', is a hydrogen atom, an alkyl, cycloalkyl, aryl, alkenyl, alkylaryl, arylalkyl, or arylalkenyl group having from 1 to 40 carbon atoms, and two R''' can join together to form a ring.

Chemical Formula 5 is as follows:

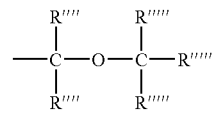

wherein each R'''', which can be the same as or different, is a hydrogen atom, an alkyl, cycloalkyl, aryl, alkenyl, alkylaryl, arylalkyl, or arylalkenyl group having from 1 to 40 carbon atoms; each R''''', which can be the same as or different, is a hydrogen atom, an alkyl, cycloalkyl, aryl, alkenyl, alkylaryl, arylalkyl, or arylalkenyl group having from 1 to 40 carbon atoms, and two neighboring R''''' can join together to form a ring, provided that when at least one of the R'''' is a hydrogen atom, then none of the R''''' is a hydrogen atom, and when at least one of the R''''' is a hydrogen atom, then none of the R'''' is a hydrogen atom.

Preferably, in Chemical Formula 1 or Chemical Formula 2 at least one of the hydrogen atoms of $R^1$, $R^2$, and D is substituted by a group represented by Chemical Formula 6.

Chemical Formula 6 is as follows:

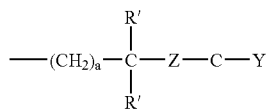

wherein Z is an oxygen atom or sulfur atom; each R', which can be the same or different, is a hydrogen atom, an alkyl, cycloalkyl, aryl, alkenyl, alkylaryl, arylalkyl, or arylalkenyl group having from 1 to 20 carbon atoms, and two R' can join together to form a ring; Y is a hydrogen atom, an alkyl, cycloalkyl, aryl, alkenyl, alkylaryl, arylalkyl, arylalkenyl, alkoxy, aryloxy, alkylthio, or arylthio group having from 1 to 20 carbon atoms, a phenyl, or a substituted phenyl, and Y and R' can join together to form a ring; and a is an integer of 4 to 8, provided that when Z is a sulfur atom, then Y is an alkoxy or aryloxy, and when Y is not alkoxy or aryloxy, Z is an oxygen atom.

More preferably, in the above Chemical Formula 6, Y is a hydrogen atom, an alkyl, cycloalkyl, aryl, alkenyl, alkylaryl, arylalkyl, or arylalkenyl group having from 1 to 20 carbon atoms, or a phenyl, either substituted or unsubstituted.

Most preferably, in the above Chemical Formula 6, Y is t-butyl.

When Y consists of only carbon and hydrogen atoms without a heteroatom such as oxygen, the supported catalyst is the most active for olefin polymerization.

In addition, the metallocene compound of the present invention can be preferably represented by Chemical Formula 7:

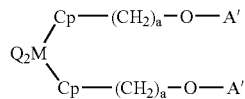

wherein M is a transition metal of Group 4'; Cp denotes a cyclopentadienyl ring unsubstituted or substituted by hydrogen, alkyl, cycloalkyl, aryl, alkenyl, alkylaryl, arylalkyl or arylalkenyl group; Q, which can be the same or different, is a halogen atom, an alkyl, alkenyl, aryl, alkylaryl, or arylalkyl group having 1 to 20 carbon atoms, or an alkylidene group having 1 to 20 carbon atoms; A' is methoxymethyl, t-butoxymethyl, tetrahydropyranyl, tetrahydrofuranyl, 1-ethoxyethyl, 1-methyl-1-methoxyethyl, or t-butyl; and a is an integer of 4 to 8.

Also, the present invention provides a supported metallocene catalyst using the above metallocene compounds and an olefin polymerization process using the supported metallocene catalysts.

The metallocene compounds in this invention are preferred for the preparation of supported catalyst due to the presence of a suitable ligand functional group such as acetal, ketal, tertiary alkoxyalkyl, benzyloxyalkyl, substituted benzyloxyalkyl, monothioacetal or monothioketal. These ligands can be introduced by replacing at least one of the hydrogen atoms of $R^1$, $R^2$, or D of the group of Chemical Formula 1 or Chemical Formula 2 with a group represented by Chemical Formula 3, Chemical Formula 4, or Chemical Formula 5.

Examples of metallocene compounds of preferred embodiments include, but are not limited to those having the following structures:

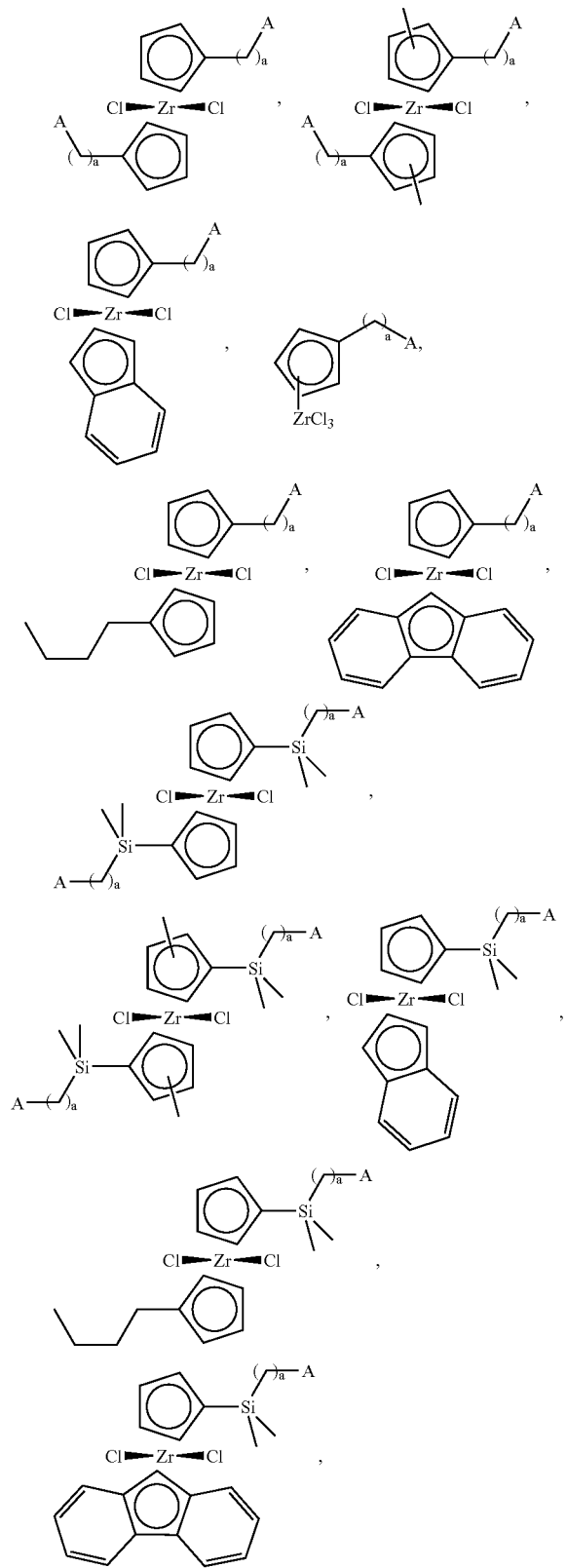

-continued

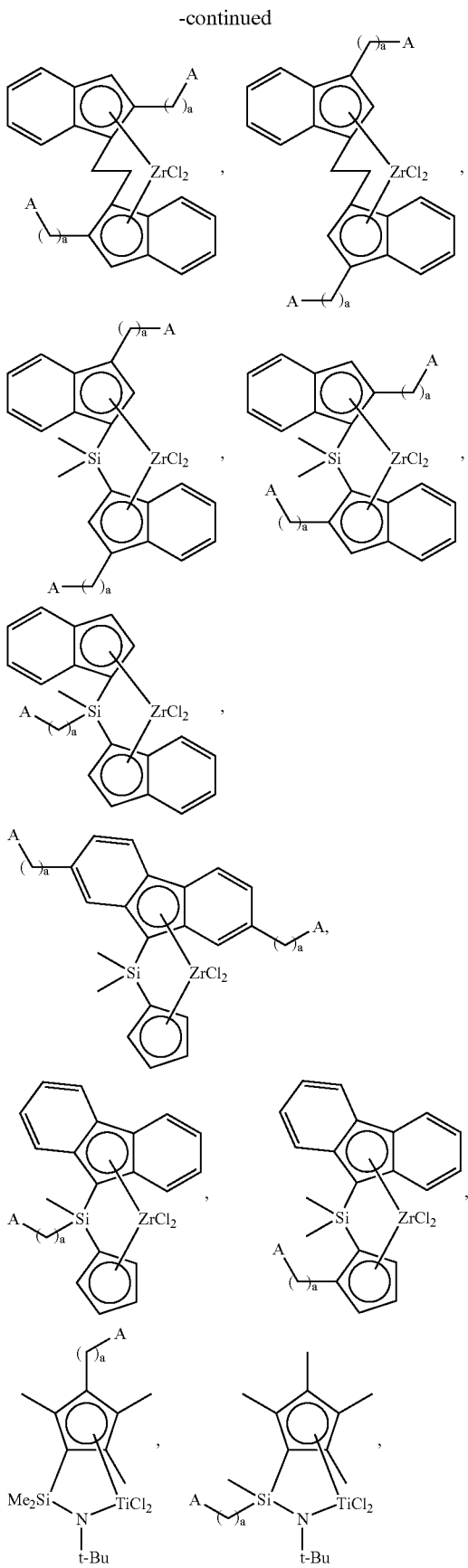

-continued

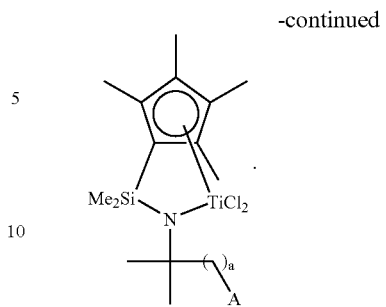

wherein A is the functional group OA' (wherein A' is an methoxymethyl, methylthiomethyl, t-butylthiomethyl, benzyloxymethyl, t-butoxymethyl, tetrahydropyranyl, 1-methoxycyclohexyl, tetrahydrofuranyl, 1-ethoxyethyl, 1-methyl-1-methoxyethyl, 1-methyl-1-benzyloxyethyl, t-butyl, diphenylmethyl, or triphenylmethyl), or A is the functional group having one of the following structures, wherein R is a hydrocarbyl group having 1 to 40 carbons:

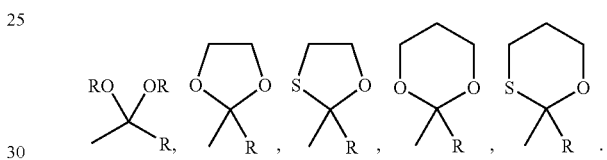

In the preferred embodiments, the substituent A' is preferably methoxymethyl, t-butoxymethyl, tetrahydropyranyl, tetahydrofuranyl, 1-ethoxylethyl, 1-methyl-1-methoxyethyl, or t-butyl, and more preferably t-butyl. When X is t-butyl—a group consisting of only carbon and hydrogen without a heteroatom such as an oxygen—its supported catalyst is the most active for olefin polymerization when compared to supported catalysts containing other groups.

In the above structures, a is an integer of from 1 to 40. The distance from the supported metallocene catalyst to the support surface is determined by the value of a. While not wishing to be bound to any particular theory, it is believed that the oxygen atom of the siloxane group on the support surface coordinates to the metal center of the catalyst, leading to a decreased activity by converting active species to inactive species. When a is 4, 5, 6, 7, or 8, the increased ring strain of the mid-size cyclic ring prohibits the coordination of the oxygen atom to the metal center. Therefore, the chance of formation of the inactive species is greatly decreased, hence a catalyst wherein a is 4 to 8 exhibits superior activity. When a is 6, the catalyst is the most active and hence the most preferable.

The metallocene compounds of preferred embodiments can be synthesized by conventional methods. That is, a substituted cyclopentadienyl group with a suitable functional group such as acetal, ketal, tertiary alkoxyalkyl, benzyloxyalkyl, substituted benzyloxyalkyl, monothioacetal, or monothioketal can be prepared by the corresponding reaction and then reacted with zirconium tetrachloride.

The cyclopentadienyl compound containing a functional group such as acetal, ketal, tertiary alkoxyalkyl, benzyloxyalkyl, substituted benzyloxyalkyl, monothioacetal, or monothioketal is prepared by the reaction of NaCp (sodium cyclopentadienide) with an organic compound containing both a halogen atom and the functional group listed above.

The organic compounds containing both a halogen atom and a functional group such as acetal, ketal, tertiary alkoxyalkyl, benzyloxyalkyl, substituted benzyloxyalkyl, monothioacetal, or monothioketal can be synthesized from compounds containing both the halogen atom and another functional groups such as aldehyde, ketone, or alcohol according to the methods described in "The Protective Group in Organic Synthesis" by T. W. Greene and P. G. M. Wuts. However, the synthesis of the compounds is not limited to the method described above, and any suitable synthesis may be employed. Nonlimiting examples of suitable syntheses are provided in Reaction Formulas 6 through 8.

Reaction Formula 6

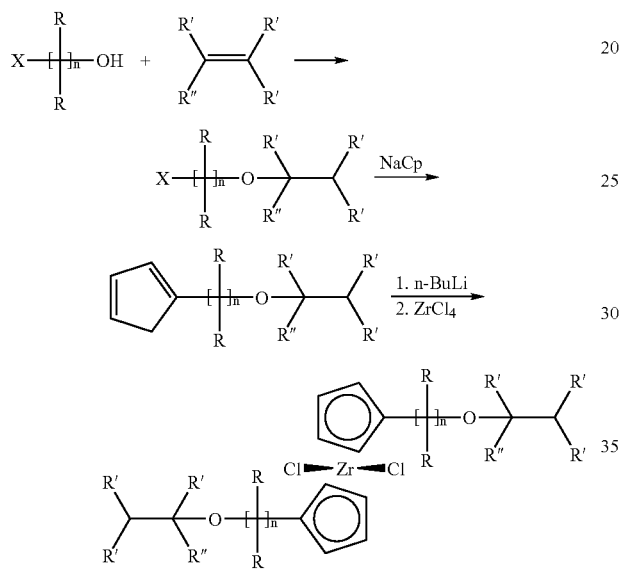

Reaction Formula 7

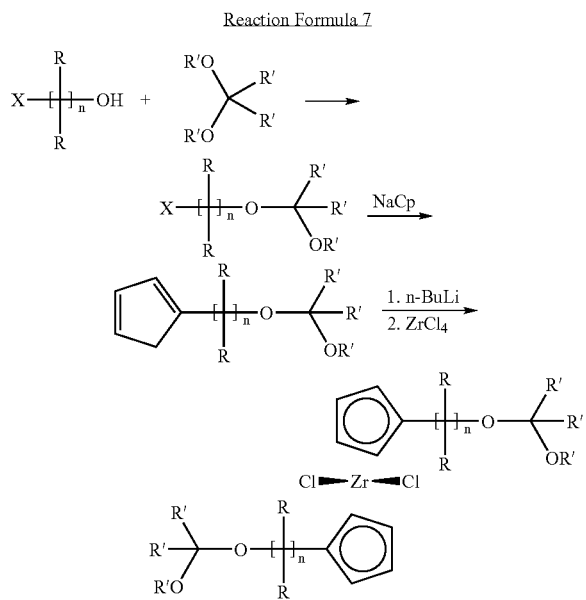

Reaction Formula 8

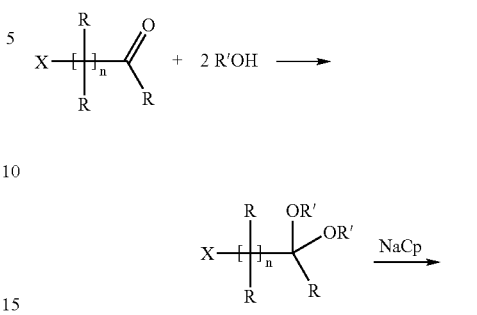

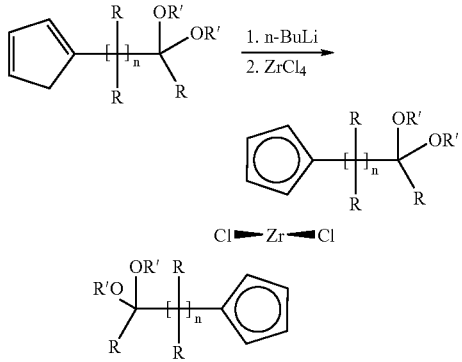

In Reaction Formulas 6 through 8, X is halogen; each R and R', which can be same or different, is a hydrogen atom, an alkyl, cycloalkyl, aryl, alkenyl, alkytaryl, arylalkyl, or arylalkenyl group, and two R' can join together to form a ring; and R" is an alkoxy, aryloxy, alkyl, cycloalkyl, aryl, alkenyl, alkylaryl, arylalkyl, or arylalkenyl group, and R" can join together to form a ring with R'.

The supported metallocene catalysts of the preferred embodiments are prepared by the reaction of the metallocene compound described above with a dehydroxylated silica calcined above about 600° C., more preferably above about 625, 650, 675, 700, 725, 750, or 775° C., and most preferably above about 800, 825, 850, 875, 900, 925, 950, 975, or 1000° C. or higher. The silica calcined above 600° C. has a highly reactive siloxane group which can react with a compound containing an alkoxysilane group, as depicted in Reaction Formula 3. The silica support employed in the preparation of supported catalysts of the preferred embodiments preferably contains hydroxyl groups in an amount of less than about 0.5 mmol/g silica, more preferably less than about 0.4, 0.3, 0.2, or 0.1 mmol/g silica. The supported catalyst exhibits superior activity when a silica support contains hydroxyl groups in an amount of less than 0.5 mmol/g silica.

The reactivity of dehydroxylated silica containing the highly reactive siloxane group towards acetal, ketal, tertiary alkoxyalkyl, benzyloxyalkyl, substituted benzyloxyalkyl, monothioacetal, or monothioketal has not been heretofore reported. This reaction leads to a new chemical bond by the cleavage of the C—O bond in the above-mentioned functional groups.

The catalysts of preferred embodiments are prepared using the reaction of the dehydroxylated silica containing highly reactive siloxane with an acetal, ketal, tertiary alkoxyalkyl, benzyloxyalkyl, substituted benzyloxyalkyl, monothioacetal, or monothioketal group, which are typically employed as protecting groups for alcohol, aldehyde, or ketone in conventional reactions. The C—O bond in the functional group mentioned above can be easily cleaved, transforming the functional groups back to alcohol, aldehyde, or ketone upon the cleavage of the C—O bond.

The preferred embodiments utilize the reaction of the highly reactive siloxane group on the silica surface with the above functional groups containing a labile C—O bond, as depicted in Reaction Formulae 9a and 9b.

Reaction Formula 9a

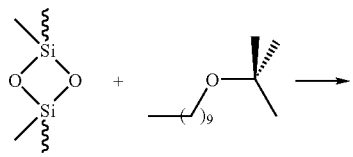

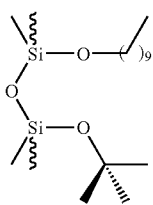

Reaction Formula 9b

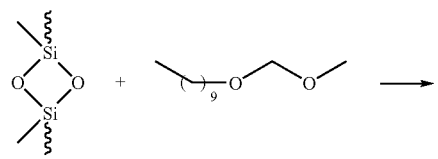

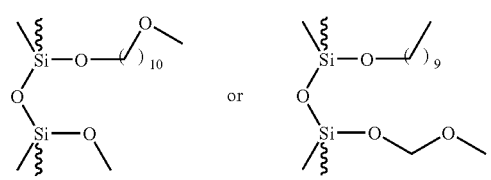

The Reaction Formulae 9a and 9b can be illustrated by the following experiment. Generally, the C—O bond in ether, acetal, or ketal functional groups is cleaved in the presence of acid, whereas it is unreactive under basic condition. That is, the tertiarybutyl decyl ether remains intact in an ethanol solution of KOH (1N) as shown in Reaction Formula 10. Under such conditions, the presence of silica that has not been dehydroxylated at a temperature above 800° C. does not affect the reactivity of tertiarybutyl decyl ether to cleavage of the C—O bond.

Reaction Formula 10

However, formation of decanol is observed for tertiarybutyl decyl ether in ethanol solution of KOH (1N) when silica dehydroxylated above 800° C. is present. This experiment shows that the C—O bond in the tertiarybutyl decyl ether is cleaved upon reaction with the silica dehydroxylated above 800° C. Unlike the C—O bond, the newly formed Si—O bond of the Si—O(CH$_2$)$_9$CH$_3$ in Reaction Formula 9a is broken easily in a basic solution, such as an ethanol solution of KOH (1N), to yield decanol. Functional groups such as acetal, ketal, tertiary alkoxy alkyl, benzyloxy alkyl, substituted benzyloxy alkyl, monothioacetal, or monothioketal each contain a C—O bond which is as reactive as that in tertiarybutyl decyl ether. They show similar reactions as depicted in Reaction Formulae 9a and 9b.

The following Reaction Formulae 11–13 provide schemes demonstrating the reaction of metallocene compounds containing functional groups such as acetal, ketal, tertiary alkoxy alkyl, benzyloxy alkyl, substituted benzyloxy alkyl, monothioacetal, or monothioketal with a highly reactive silica surface.

Reaction Formula 11

Dehydroxylated Silica

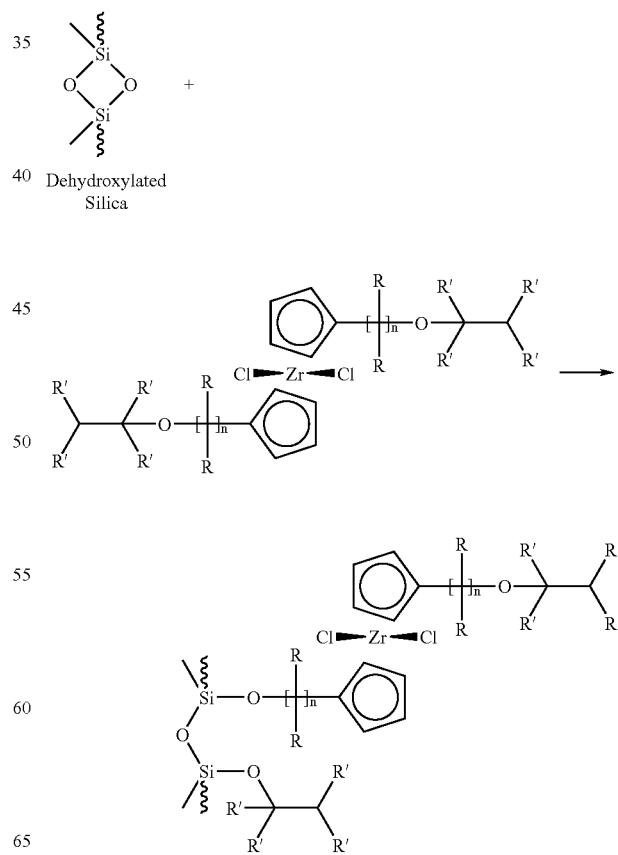

Reaction Formula 12

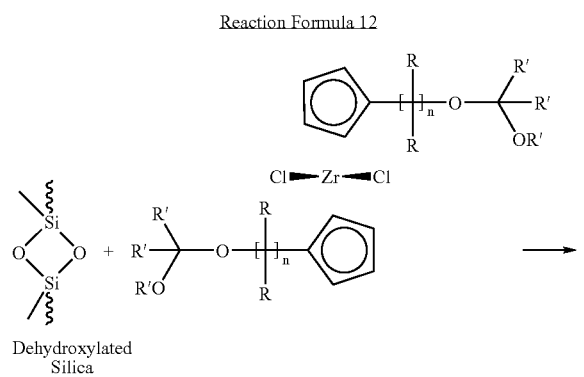

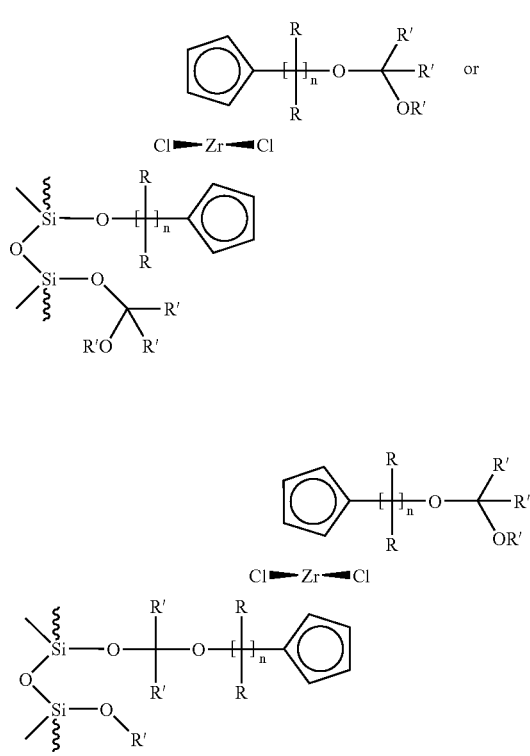

Reaction Formula 13

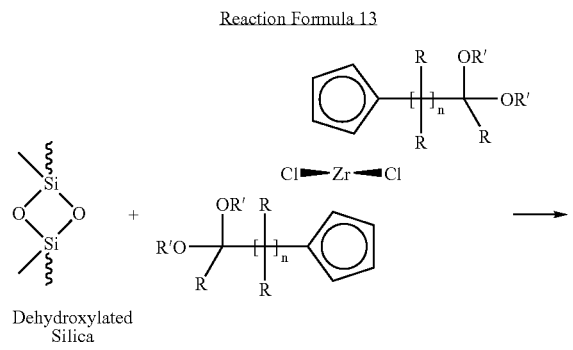

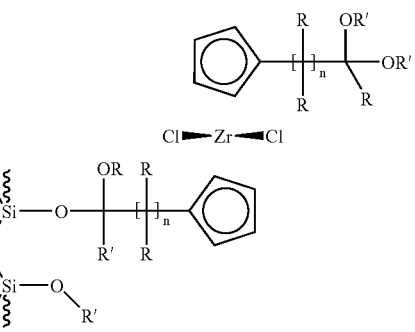

wherein each R and R', which can be same or different, are hydrogen atoms, alkyl, cycloalkyl, aryl, alkenyl, alkylaryl, arylalkyl, or arylalkenyl groups, and two R' can join together to form a ring.

In the preparation of supported metallocene catalysts of the preferred embodiments, a silica support which is fully dehydroxylated (less than 0.5 mmol hydroxyl per g silica) but which maintains its fundamental structures such as surface area, pore volume and pore size, is preferred in order to minimize side reactions during the supporting process. It is also preferable to dry the silica at a higher temperature such that more siloxane groups (and fewer hydroxyl groups) are present on the silica surface.

Suitable solvents for the impregnation process include, but are not limited to aliphatic hydrocarbon solvents such as hexane, heptane, and isobutane, aromatic hydrocarbon solvents such as toluene and benzene, chlorinated hydrocarbon solvents such as dichloromethane, ethers such as diethyl ether and tetrahydrofuran (THF), or other common organic solvents such as acetone or ethylacetate. Mixtures of solvents may also be employed. Aliphatic hydrocarbon solvents such as hexane, heptane, and isobutane are generally preferred, however.

The supporting reaction is preferably performed at a temperature of from about −30° C. to 300° C., more preferably from about 50° C. to 150° C. When the reaction temperature is 50 to 150° C., the resulting supported catalyst exhibits superior activity. A supported catalyst suitable for use in an olefin polymerization process can be prepared as a dried powder phase which is separated by filtration from a reaction solution, followed by a drying step. However, when a slurry process is employed, the supported catalyst can be prepared in the same solvent which is used for the olefin polymerization process. Then, the catalyst is separated by filtration from the solution (optionally, after several washing steps), and is used directly for the activation and polymerization reactions as a slurry without a drying step.

The supported metallocene catalyst prepared according to this method is suitable for use in an olefin polymerization process in combination with a co-catalyst having a group or groups represented by one or more of Chemical Formula 4, 5, or 6. Preferably, a co-catalyst having a group represented by Chemical Formula 4 or 5 is used.

Examples of compounds having a group represented by Chemical Formula 4 include but are not limited to methylaluminoxane, ethylaluminoxane, isobutylaluminoxane, butylaluminoxane, and the like.

Examples of metal alkyl compounds having a group represented by Chemical Formula 5 include, but are not limited to trimethylaluminum, triethylaluminum, triisobutylaluminum, tripropylaluminum, tributylaluminum, dimethylchloroaluminum, dimethylisobutylaluminum, ethyldimethylaluminum, diethylchloroaluminum, triisopropylaluminum, tri-s-butylaluminum, tricyclopentylaluminum, tripentylaluminum, triisopentylaluminum, trihexylaluminum, methyldiethylaluminum, tripentylaluminum, tri-p-tolylaluminum, dimethylaluminummethoxide, dimethylaluminummethoxide, and the like.

Examples of compounds having a group represented by Chemical Formula 6 include, but are not limited to triethylammonium tetraphenylborate, tributylammonium tetraphenylborate, trimethylammonium tetraphenylborate, tripropylammonium tetraphenylborate, trimethylammoniumtetrakis(p-tolyl)borate, triethylammoniumtetrakis(o,p-dimethylphenyl)borate, trimethylammonium tetrakis(o,p-dimethylphenyl)borate, tributylammonium tetrakis(p-trifluoromethylphenyl)borate, trimethylammonium tetrakis(p-trifluoromethylphenyl)borate, tributylammonium tetrapentafluorophenylborate, N,N-diethylaniliniumtetraphenylborate, N,N-dimethylaniliniumtetraphenyl borate, N,N-diethylanilinium tetrakispentafluorophenyl borate, diethylammonium tetrakispentafluorophenyl borate, triphenylphosphonium tetraphenylborate, trimethylphosphonium tetraphenylborate, triethylammonium tetraphenylaluminate, tributylammonium tetraphenylaluminate, trimethylammonium tetraphenylaluminate, tripropylammonium tetraphenylaluminate, trimethylammonium tetrakis(p-tolyl)aluminate, triethylammonium tetrakis(o,p-dimethylphenyl)aluminate, tributylammonium tetrakis(p-trifluoromethylphenyl) aluminate, trimethylammonium tetrakis(p-trifluoromethylphenyl) aluminate, tributylammonium tetrakispentafluorophenyl aluminate, N,N-diethylanilinium tetraphenylaluminate, N,N-dimethylaniliniumtetraphenylaluminate, N,N-diethylanilinium tetrakispentafluorophenylaluminate, diethylammonium tetrakispentafluorophenylaluminate, triphenylphosphonium tetraphenylaluminate, trimethylphosphonium tetraphenylaluminate, triethylammonium tetraphenylborate, tributylammonium tetraphenylborate, trimethylammonium tetraphenylborate, tripropylammonium tetraphenylborate, trimethylammonium tetrakis(p-tolyl)borate, tripropylammonium tetrakis(p-tolyl)borate, triethylammoniumtetrakis(o,p-dimethylphenyl)borate, trimethylammoniumtetrakis(o,p-dimethylphenyl)borate, tributylammonium tetrakis(p-trifluoromethylphenyl)borate, trimethylammonium tetrakis (p-trifluoromethylphenyl)borate, tributylammonium tetrakispentafluorophenylborate, N,N-diethylanilinium tetraphenylborate, N,N-diethylanilinium tetraphenylborate, N,N-diethylanilinium tetrakispentafluorophenylborate, diethylammonium tetrkispentafluorohenylborate, triphenylphsphonium tetraphenylborate, triphenylcarbonium tetraphenylborate, triphenylcarbonium tetraphenylaluminate, triphenylcarbonium tetrakis(p-trifluoromethylphenyl)borate, triphenylcarbonium tetrakispentafluorophenylborate, and the like.

In an olefin polymerization process utilizing the supported metallocene catalyst with the co-catalyst described above, suitable solvents include, but are not limited to aliphatic hydrocarbon solvents containing 3 to 12 carbons, such as propane, butane, isobutane, pentane, hexane, heptane, nonane, decane, and isomers thereof, aromatic hydrocarbon solvents such as toluene and benzene, chlorinated hydrocarbon solvents such as dichloromethane or chlorobenzene, or any mixtures thereof.

It is also possible to perform the olefin polymerization process in a gas phase or a bulk phase with the metallocene catalyst and the co-catalyst without employing any solvent.

Examples of olefin based monomers which are capable of polymerization by using the metallocene catalysts or supported metallocene catalysts with the co-catalysts of preferred embodiments include, but are not limited to ethylene, α-olefins, cyclic olefins, and the like, and olefinic monomers having more than two double bonds, such as diene monomers, triene monomers, polyene monomers, and the like. Specific examples of the monomers described above include, but are not limited to ethylene, propylene, 1-butene, 1-pentene, 2-butene, 2-pentene, 4-methyl-1-pentene, 1-hexene, 1-heptene, 1-octene, 1-nonene, 1-decene, 1-undecene, 1-dodecene, 1-tetradecene, 1-hexandecene, 1-icocene, norbornene, norbomadiene, ethylidenenorbornene, vinylnorbornene, dicyclopentadiene, 1,4-butadiene, 1,5-pentadiene, 1,6-hexadiene, styrene, a-methylstyrene, divinylbenzene, or 3-chloromethylstyrene, etc. Co-polymerization can be accomplished by employing more than one of these monomers.

Polymerization is preferably performed at a temperature of from about −25° C. to 500° C. and at a pressure of from 0.001 to 3000 atm. However, in certain embodiments temperatures and pressures above or below the specified ranges may also be employed. It is preferred to add co-catalyst in an amount that is about 1 to 30,000 times the metallocene compound mole content. However, in certain embodiments, a greater or lesser mole content than that specified may also be employed.

In the preferred embodiments, no particular contact order or input order of catalyst, co-catalyst, solvent, and monomer is generally preferred. That is, polymerization is done by putting the supported catalyst and co-catalyst into suspension solvents simultaneously, or the main polymerization can be performed after either the activation reaction or pre-polymerization reaction.

The main polymerization can be conducted in a suitable suspension solution by introducing the monomers. It may also be conducted in the gas phase or in the bulk phase without diluent. Pre-polymerized catalyst is prepared from the supported catalyst mixed with the co-catalyst under suitable olefin polymerization conditions of temperature and pressure. The pre-polymerized catalyst is then separated either by filtration or decantation. Activated catalyst can be obtained by the same method of pre-polymerization reaction, but without olefin present. Treatment of the supported catalyst with an organic aluminum compound before the polymerization process can reduce the amount of methylaluminoxane employed in the polymerization reaction.

Although the preferred embodiments are illustrated in detail by the following examples, the preferred embodiments are not limited to these examples.

EXAMPLES

Organic reagents and solvents for the catalyst synthesis and polymerization processes were purchased from Aldrich or Merck and then refined according to standard methods. High purity ethylene gas (from Applied Gas Technology) was polymerized after passing through a moisture scavenging and oxygen-scavenging filter. Reproducibility was maintained by performing all stages of catalyst synthesis, impregnation, and polymerization under an inert gas atmosphere.

The catalysts were analyzed by Nuclear Magnetic Resonance (NMR) spectroscopy employing a 300 MHz Bruker instrument. Bulk density was determined according to the ISO R 60 and DIN 53466 standards with an Apparent Density Tester 1132 made by Prüftechnic. Molecular weight and distribution of molecular weight were determined using gel permeation chromatography (GPC) on a Waters Model 150CV+ GPC instrument. The data were obtained at 140° C. with trichlorobenzene as a solvent and were analyzed using a polystyrene analyzing curve. Microscope images were obtained on a Nikon OPTIPHOT2-POL.

Example 1

Synthesis of [methoxymethyl-O—$(CH_2)_6$—$C_5H_4$]$_2ZrCl_2$

6-Chlorohexyl-1-methyl-1-methoxyethyl ether was synthesized from 6-chlorohexanol and 2-methoxypropene by a literature method (Klug, et al. *J. Am. Chem. Soc.* 94, 7827, (1972)). To this, one equivalent of NaCp (2.0 M in THF) was added and stirred overnight. Water was added to this solution and the organic layer was extracted and dried with $MgSO_4$. The solvent was removed and methoxymethyl-O—$(CH_2)_6$—$C_5H_5$ was obtained by vacuum distillation (approximately 80° C./0.1 mmHg; yield was 56% based on 6-chlorohexanol).

1.349 g of the methoxymethyl-O—$(CH_2)_6$—$C_5H_5$ thus obtained was dissolved in 5 mL of THF and cooled down to −40° C. To this solution, one equivalent of $^n$BuLi (in hexane) was added and the solution was stirred for three hours with a slow warming to room temperature. This solution was then added to a flask containing 0.5 equivalents of $ZrCl_4(THF)_2$ at 55° C. and agitated for forty hours. The solvent was removed by a distillation and 30 mL of hexane was added. Filtration at 55° C. followed by removal of hexane gave 1.711 g of the product (yield: 92%). This product was employed in the preparation of a supported catalyst without a further purification step.

Spectroscopic analysis of the product by NMR was as follows: $^1$H NMR (δ, 300 MHz, $CDCl_3$): 6.28 (t, J=2.7 Hz, 2H), 6.19 (t, J=2.7 Hz, 2H), 4.61 (s, 2H), 3.50 (t, J=6.5 Hz, 2H), 3.35 (s, 3H), 2.63 (t, J=8 Hz, 2H), and 1.6–1.3 (m, 8H); $^{13}$C NMR (δ, $CDCl_3$): 135.00, 116.69, 112.17, 96.38, 67.72, 55.09, 30.58, 30.09, 29.63, 29.09, and 25.95.

Example 2

Synthesis of [1-methyl-1-methoxyethyl-O—$(CH_2)_6$—$C_5H_4$]$_2ZrCl_2$ 1-methyl-1-methoxyethyl-O—$(CH_2)_6$—Cl was prepared from 6-chlorohexanol by a literature method (*J. Am. Chem. Soc.* 7827, (1972)). 1-methyl-1-methoxyethyl-O—$(CH_2)_6$—$C_5H_5$ was obtained from the reaction with NaCp by the method described above (yield: 44%).

The product was obtained by the same method described above, except that zirconation was conducted at room temperature. The resulting compound was relatively stable in a solution state but was unstable in the absence of solvent.

Spectroscopic analysis of the product by NMR was as follows: $^1$H NMR (δ, 270 MHz, $CDCl_3$): 6.28 (t, J=3.0 Hz, 2H), 6.19 (t, J=3.0 Hz, 2H), 3.37 (t, J=6.8 Hz, 2H), 3.18 (s, 3H), 2.63 (t, J=8 Hz, 2H), 1.6–1.3 (m, 8H), and 1.33 (6H).

Example 3

Synthesis of [tetrahydropyranyl-O—$(CH_2)_6$—$C_5$]$_2ZrCl_2$

Tetrahydropyranyl-O—$(CH_2)_6$—Cl was prepared from 6-chlorohexanol by a literature method (*Synthesis* 618, (1979)). Tetrahydropyranyl-O—$(CH_2)_6$—$C_5H_5$ was obtained from a reaction with NaCp by the method described above (yield: 58%).

The product was obtained by the same method described above (yield: 58%).

Spectroscopic analysis of the product by NMR was as follows: $^1$H NMR (δ, 300 MHz, $CDCl_3$): 6.28 (t, J=2.6 Hz, 2H), 6.19 (t, J=2.6 Hz, 2H), 4.6–4.5 (m, 1H), 3.9–3.8 (m, 1H), 3.71 (dt, J=9.6 Hz, 1H), 3.5–3.4 (m, 1H), 3.36 (dt, 9.6 Hz, 6.8 Hz, 1H), 2.62 (t, J=8 Hz, 2H), and 1.9–1.2 (m, 14H); $^{13}$C NMR (δ, $CDCl_3$): 135.01, 116.66, 112.23, 98.86, 67.52, 62.36, 30.77, 30.60, 30.10, 29.64, 29.12, 25.98, 25.48, and 19.70.

Example 4

Synthesis of [1-ethoxyethyl-O—$(CH_2)_6$—$CH_5H_4$]$_2ZrCl_2$

1-Ethoxyethyl-O—$(CH_2)_6$—Cl was prepared from 6-chlorohexanol by a literature method (*Chem. Ind.* (*London*) 1710, (1964)), and 1-ethoxyethyl-O—$(CH_2)_6$—$C_5H_5$ was obtained from a reaction with NaCp by the method described above (yield: 69%).

The product was obtained by the same method described above (yield: 80%).

Spectroscopic analysis of the product by NMR was as follows: $^1$H NMR (δ, 300 MHz, $CDCl_3$): 6.29 (t, J=2.6 Hz, 2H), 6.20 (t, J=2.6 Hz, 2H), 4.67 (q, J=5.3 Hz, 1H), 3.7–3.3 (m, 4H), 2.63 (t, J=8 Hz, 2H), 1.7–1.2 (m, 8H), 1.29 (d, J=5.3 Hz, 3H), and 1.20 (t, J=7.1 Hz, 3H); $^{13}$C NMR (δ, $CDCl_3$): 134.93, 116.62, 112.14, 99.47, 65.10, 60.63, 30.52, 30.03, 29.72, 29.06, 25.93, 19.83, and 15.27.

Example 5

Synthesis of [t-butyl-O—$(CH_2)_6$—$C_5H_4]_2ZrCl_2$

Tertiary-butyl-O—$(CH_2)_6$—Cl was prepared from 6-chlorohexanol by a literature method (*Tetrahedron Lett.* 2951, (1988)), and t-butyl-O—$(CH_2)_6$—$C_5H_5$ was obtained from a reaction with NaCp by the same method described above (yield: 60%, b.p. approximately 80° C. at 0.1 mmHg).

The product was obtained by the same method described above (Yield: 92%).

Spectroscopic analysis of the product by NMR was as follows: $^1$H NMR (δ, 300 MHz, $CDCl_3$): 6.28 (t, J=2.6 Hz, 2H), 6.19 (t, J=2.6 Hz, 2H), 3.31 (t, J=6.6 Hz, 2H), 2.62 (t, J=8 Hz), 1.7–1.3 (m, 8H), and 1.17 (s, 9H); $^{13}$C NMR (δ, $CDCl_3$): 135.09, 116.66, 112.28, 72.42, 61.52, 30.66, 30.61, 30.14, 29.18, 27.58, and 26.00.

Example 6

Preparation of the Supported Catalyst

Silica support (XPO 2412 from Grace Davison) was dehydroxlated at 800° C. under vacuum.

To separate glass reactors charged with 1.0 g of silica and 20 mL of hexane were added 10 mL of hexane solution containing 100 mg of the catalysts prepared in the above Examples 1 through 5. The solutions were stirred for 3 hours at 85° C. and hexane was removed by a decantation. The remaining hexane was removed under reduced pressure to yield supported catalyst.

Example 7

Polymerization

In a dry box, 100 mg of the supported catalyst was weighed and transferred to a glass reactor. The glass reactor was sealed, removed from the dry box, and filled with 50 mL of hexane and MAO solution dissolved in either hexane solution or heptane solution (1.0 mmol of Al). The solution was stirred for 30 minutes at 40° C. and then pre-polymerized with 30 psig ethylene atmosphere for 30 minutes at room temperature.

The pre-polymerized catalyst prepared as described above and 660 mL of hexane solution containing 1.0 mmol of triethylaluminum were transferred to a Büchi reactor under an inert gas atmosphere. Polymerization was performed at 80° C. for 60 minutes under 130 psig atmosphere of ethylene. Upon the completion of the polymerization reaction, ethylene was removed by ventilation. The resulting polymer was filtered and dried at 80° C. in an oven.

Table 1 provides activity, bulk density, molecular weight, and distribution of molecular weight for the catalysts prepared above. Bulk density of the polymer was 0.36~0.39 g/mL and no fouling in the reactor was observed.

Figure 2:
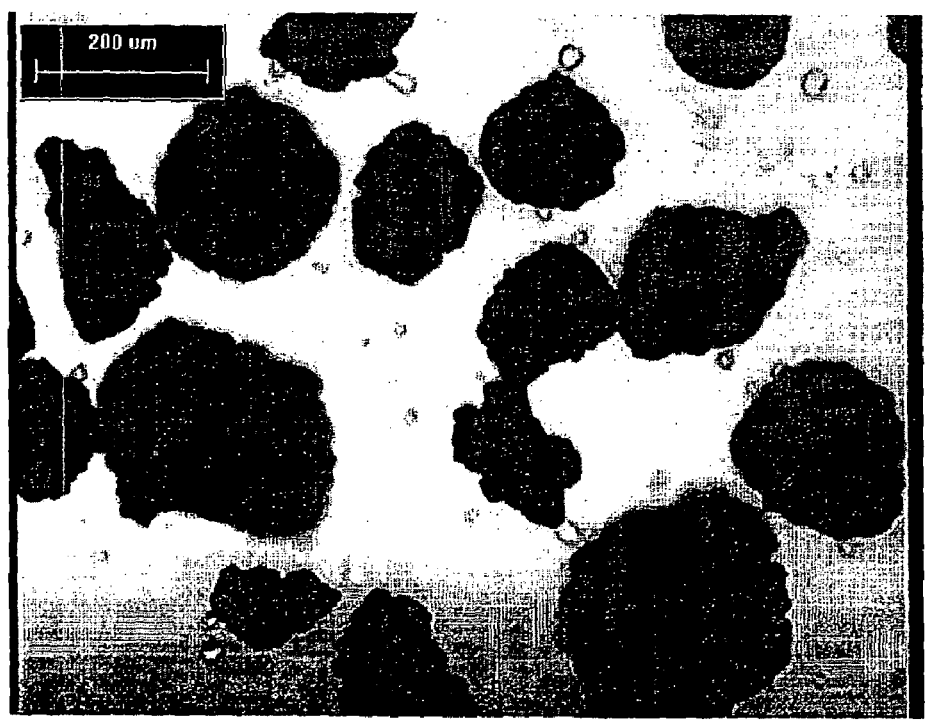
FIG. 2 is an optical microscope photograph of polymer morphology (40 times magnified), wherein the polymer was prepared using the catalyst of Example 5 supported on a silica surface.

FIG. 1 shows the morphology of the supported catalyst and FIG. 2 shows the morphology of the polymer prepared from the supported catalyst prepared from [t-butyl-O—$(CH_2)_6$—$C_5H_4]_2ZrCl_2$. FIGS. 1 and 2 show the similarities of the morphology of the polymer and that of the catalyst. It was also observed that the morphology of polymers obtained from catalysts listed in Table 1 was similar to that of FIG. 2.

Comparative Example 1

Figure 3:
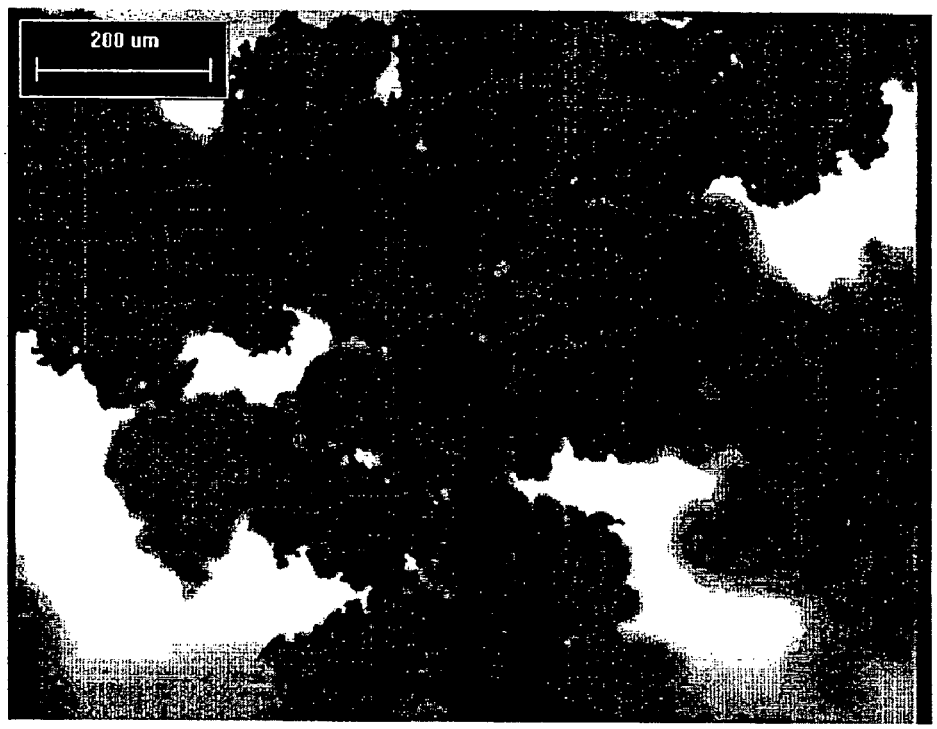
FIG. 3 is an optical microscope photograph of polymer morphology (40 times magnified), wherein the polymer was prepared using the catalyst of Comparative Example 1 supported on a silica surface.

Preparation of a supported catalyst, pre-polymerization, and main polymerization were carried out according to Examples 6 and 7 using bis(octylcyclopentadienyl)zirconium dichloride, which has no functional group capable of reaction with silica. The yield was 51 g and a severe fouling was observed during the preliminary and main polymerization. The morphology was poor and the bulk density was 0.04 g/mL (Table 1). FIG. 3 shows its irregular morphology.

Comparative Example 2

The catalyst compound [2-ethoxyethyl-O—$(CH_2)_6$—$C_5H_4]_2ZrCl_2$ which is similar to a catalyst shown in examples of U.S. Pat. No. 5,814,574 and No. 5,767,209 was prepared by the literature method (*J. Organomet. Chem.* Vol. 552, 313, (1998)) published by this inventor. This compound has a primary alkyl chain which shows relatively high Lewis basicity, and has four oxygen atoms. The presence of four oxygen atoms results in satisfactory binding to an inorganic support by a Lewis acid-base interaction, but the C—O bond is difficult cleave. This catalyst was supported by the same method described in Example 6 and then preliminary and main polymerization were performed.

Figure 4:
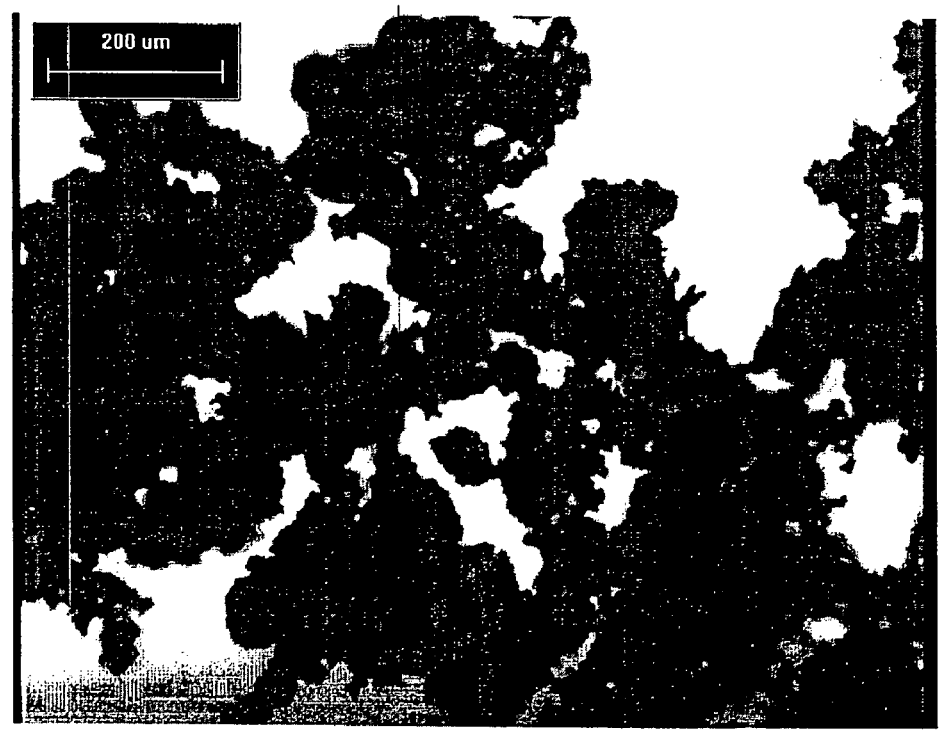
FIG. 4 is an optical microscope photograph of polymer morphology (40 times magnified), wherein the polymer was prepared using the catalyst of Comparative Example 2 supported on a silica surface.

Only 7 g of polymer was obtained and severe fouling was observed. The morphology was very irregular and the bulk density was only 0.08 g/mL. FIG. 4 shows its poor morphology.

Comparative Example 3

Polymerization was performed with [2-ethoxyethyl-O—$(CH_2)_6$—$C_5H_4]_2ZrCl_2$ which was bound to and supported on $MgCl_2$. 26.5 mg of [2-ethoxyethyl-O—$(CH_2)_6$—$C_5H_4]_2ZrCl_2$ was mixed with 600 mg of ball-milled anhydrous magnesium dichloride, and the mixture was agitated for two hours in 30 mL of hexane. Hexane was removed by decantation and the supported catalyst was washed again. Remaining hexane was removed under reduced pressure. 100 mg of the supported catalyst was transferred to a glass reactor and 250 mL of hexane and 1.6 mL of MAO solution were added. The solution was stirred for 5 minutes at 80° C. Polymerization was performed in an atmosphere of 40 psig ethylene for an hour. Reactor fouling and irregular morphology were observed. 7.4 g of polyethylene was obtained with a bulk density of 0.10 g/mL.

TABLE 1

| Classification | Compound | Activity (g) | Bulk density (g/mL) | Mw ($\times 10^{-3}$) | Mw/Mn |
|---|---|---|---|---|---|
| Example 1 | [methoxymethyl-O-$(CH_2)_6$-$C_5H_4]_2ZrCl_2$ | 53 | 0.39 | 241 | 2.5 |
| Example 2 | [1-methyl-1-methoxyethyl-O-$(CH_2)_6$-$C_5H_4]_2ZrCl_2$ | 70 | 0.36 | 248 | 2.5 |
| Example 3 | [tetrahydropyranyl-O-$(CH_2)_6$-$C_5H_4]_2ZrCl_2$ | 80 | 0.38 | 240 | 2.4 |
| Example 4 | [1-ethoxyethyl-O-$(CH_2)_6$-$C_5H_4]_2ZrCl_2$ | 79 | 0.37 | 234 | 2.5 |
| Example 5 | [t-butyl-O-$(CH_2)_6$-$C_5H_4]_2ZrCl_2$ | 101 | 0.36 | 226 | 2.6 |
| Comparative Example 1 | [$CH_3$-$(CH_2)_7$-$C_5H_4]_2$-$ZrCl_2$ | 51 | 0.04 | 290 | 2.5 |
| Comparative Example 2 | [2-ethoxyethyl-O-$(CH_2)_6$-$C_5H_4]_2ZrCl_2$ | 7 | 0.08 | 377 | 2.6 |

As can be seen from the above Table 1, the supported metallocene catalysts prepared from the metallocene compounds of the preferred embodiments that comprise a functional group such as 1-methyl-1-methoxyethyl, tetrahydropyranyl, 1-ethoxylethyl, and t-butyl showed superior activity for olefin polymerization when compared to those comprising other functional groups.

Example 8

The Formation of a New Chemical Bond on the Surface Upon Breakage of the C—O Bond The following model experiment was conducted to demonstrate the formation of a new chemical bond on the silica surface upon the breakage of the C—O bond, which is one of the major characteristics of this invention.

The dehydroxylated silica prepared in Example 5 was treated with tertiary butyl decyl ether (t-Butyl-O—$(CH_2)_9$—$CH_3$) which was prepared from decanol by a literature method (*Tetrahedron Lett.* 2951 (1988)). The suspension was stirred for two hours at 90° C. and unreacted tertiary butyl decyl ether was removed under reduced pressure. For a complete removal of unreacted tertiary butyl decyl ether, the powder was dried at 150° C. for a day under a reduced pressure of 1 torr. 0.5 g of this powder was added to 5 mL of an ethanol solution of KOH (1N) and stirred for five hours at room temperature. The resulting solution was transferred to a separatory funnel containing diethyl ether and water, and the diethyl ether layer was separated. This organic layer was dried with MgSO$_4$, and ether was removed to give 15 mg of organic compound. $^1$H NMR analysis showed that most of the compound was decanol.

To see if the C—O bond of the tertiary butyl decyl ether was cleaved under the above basic condition i.e., an ethanol solution of KOH (1N) or an ethanol solution of KOH (1N) containing silica, the following experiment was performed. When tertiary butyl decyl ether was reacted with 5 mL of an ethanol solution of KOH (1N) at room temperature for a day, TLC analysis showed the presence of the tertiary butyl decyl ether without any change. There was no change in the tertiary butyl decyl ether at 80° C. for a day of reflux in the ethanol solution of KOH. Reflux of the solution with 0.5 g of silica for a day at 80° C. yielded unreacted tertiary butyl decyl ether on the TLC analysis.

This experiment showed the C—O bond is cleaved only when the tertiary butyl decyl ether is treated with silica dehydroxylated at 800° C.

The metallocene compounds of the preferred embodiments are strongly supported on the inorganic support due to the strong chemical bond between the ligand of the metallocene compound and the silica surface, which results in minimized leaching of the catalyst during the activation process. Therefore, when the supported catalyst of the preferred embodiments is employed in a slurry or a gas phase process, the process proceeds without fouling in the reactor, and the bulk density of the polymer produced is better defined than that produced by the conventional method.

Examples 9 and 10 and Comparative Example 4

Effect of Carbon Distance Between Cp and Functional Group on Activity of the Catalyst The effects of carbon distance between Cp and functional group on the activity of a supported catalyst were investigated. Compounds of the following structure with carbon lengths (n) of 2, 4, 6 and 8 were respectively prepared:

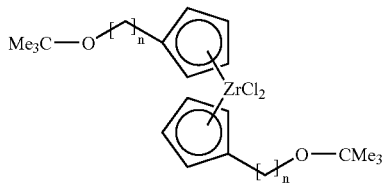

Example 9

Synthesis of [t-butyl-O—(CH$_2$)$_4$—C$_5$H$_4$]ZrCl$_2$

[t-Butyl-O—(CH$_2$)$_4$—C$_5$H$_4$]$_2$ZrCl$_2$ was prepared by the same method as in Example 5, except that 4-chlorobutanol was used.

Spectroscopic analysis of the product by NMR was as follows: $^1$H NMR (400 MHz, CDCl$_3$): δ6.29 (t, 2H), 6.21 (t, 2H), 3.34 (t, 2H), 2.65 (t, 2H), 1.59 (m, 4H), 1.17 (s, 9H); $^{13}$C NMR (400 MHz, CDCl$_3$): δ135.6, 117.6, 113.1, 73.3, 62.0, 31.0, 30.7, 28.3.

Example 10

Synthesis of [t-butyl-O—(CH$_2$)$_8$—C$_5$H$_4$]$_2$ZrCl$_2$

[t-Butyl-O—(CH$_2$)$_8$—C$_5$H$_4$]$_2$ZrCl$_2$ was prepared by the same method as in Example 5, except that 8-chlorooctanol was used.

Spectroscopic analysis of the product by NMR was as follows: $^1$H NMR (400 MHz, CDCl$_3$): δ6.29 (br s, 2H), 6.20 (br s, 2H), 3.31 (m, 2H), 2.61 (m, 2H), 1.52 (br m, 4H), 1.29 (br s, 8H), 1.18 (s, 9H); $^{13}$C NMR (400 MHz, CDCl$_3$): δ135.8, 117.4, 113.1, 73.1, 62.4, 31.4, 30.9, 30.2, 30.1, 30.0, 28.3, 27.0.

Comparative Example 4

Synthesis of [t-butyl-O—(CH$_2$)$_2$—C$_5$H$_4$]$_2$ZrCl$_2$

[t-Butyl-O—(CH$_2$)$_2$—C$_5$H$_4$]$_2$ZrCl$_2$ was prepared by the same method as in Example 5, except that 2-chloroethanol was used.

Spectroscopic analysis of the product by NMR was as follows: $^1$H NMR (400 MHz, CDCl$_3$): δ6.30 (s, 4H), 3.42 (t, 2H), 2.83 (t, 2H), 1.16 (s, 9H); $^{13}$C NMR (400 MHz, CDCl$_3$): δ132.4, 118.2, 113.5, 73.7, 62.4, 32.4, 28.3.

Example 11

Preparation of the Supported Catalyst

Supported catalysts (n=2, 4, 6, 8) were prepared by the same method as in Example 6 using the catalysts from Example 5, Example 9, Example 10, and Comparative Example 4, respectively. In this preparation, molar ratios of zirconium to silica (1 g) were all equivalent to 0.165 mmol.

Polymerization

Hexane (500 mL) and a MAO solution were fed into a 1 L glass reactor. Zirconium solution (Al/Zr=500) was then injected into the reactor, and the mixture was heated to 80° C. for 5 min. Polymerization was performed by a continuous feed of ethylene at 4 bar to the reactor for 30 min. The reaction was stopped by addition of MeOH. Concentrated HCl was added, and the suspension was stirred overnight. After filtration, the polymer was dried under vacuum at 80° C. The yield, activity, molecular weights, and molecular weight distributions ($M_w/M_n$) of the polymers were then measured, as shown in Table 2.

TABLE 2

| Example | Carbon Length (n) | Yield (g) | Activity[1] | Mw | Mw/Mn |
|---|---|---|---|---|---|
| Comparative Example 4 | C2 | Trace | — | — | — |
| Example 9 | C4 | 2.50 | 100 | 133,780 | 2.60 |
| Example 5 | C6 | 5.80 | 232 | 147,390 | 2.61 |
| Example 10 | C8 | 2.74 | 110 | 92,830 | 3.02 |

[1]g PE/g Cat · hr

As can be seen from the data in Table 2, there exists an optimum distance between Cp and a functional group to produce an active supported catalyst. When carbon chain length (n) is 6, the resulting supported catalyst (e.g., as in Example 5) is most active for ethylene polymerization. In cases wherein the carbon chain length is less than 4 or more than 8, activities may be hampered by catalyst deactivation reactions. Therefore, it can be concluded that metallocene compounds having 4 to 8 carbon chain lengths are the most preferred structures.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein, are hereby incorporated by reference in their entirety.

What is claimed is:

1. A supported metallocene catalyst of the following formula obtained by using a dehydroxylated silica support including a hydroxyl group amount of less than 0.5 mmol/g silica:

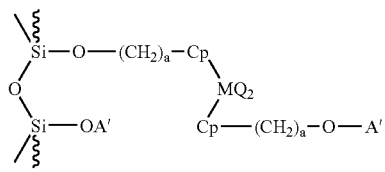

wherein M comprises a transition metal of Group 4;

Cp, which are the same or different, comprise a cyclopentadienyl ring, wherein the cyclopentadienyl ring is unsubstituted or substituted by a moiety selected from the group consisting of alkyl, cycloalkyl, aryl, alkenyl, alkylaryl, arylalkyl, and arylalkenyl;

Q, which are the same or different, comprise halogen or a moiety comprising from 1 to 20 carbon atoms, wherein the moiety is selected from the group consisting of alkyl, alkenyl, aryl, alkylaryl, arylalkyl, and alkylidene;

A', which are the same or different, are selected from the group consisting of methoxymethyl, t-butoxymethyl, tetrahydropyranyl, tetrahydrofuranyl, 1-ethoxyethyl, 1-methyl-1-methoxyethyl, and t-butyl; and a comprises an integer of from 4 to 8.

2. The supported metallocene catalyst according to claim 1, wherein A' comprises t-butyl.

3. The supported metallocene catalyst according to claim 1, wherein a is 6.

4. A method for preparing a supported metallocene catalyst, the method comprising the step of:

reacting a metallocene compound of Chemical Formula 7:

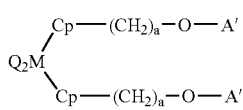

with a dehydroxylated silica support of the following formula including a hydroxyl group amount of less than 0.5 mmol/g silica:

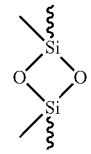

in an organic solvent, wherein:

M comprises a transition metal of Group 4;

Cp, which are the same or different, comprise a cyclopentadienyl ring, wherein the cyclopentadienyl ring is unsubstituted or substituted by a moiety selected from the group consisting of alkyl, cycloalkyl, aryl, alkenyl, alkylaryl, arylalkyl, and arylalkenyl;

Q, which are the same or different, comprise halogen or a moiety comprising from 1 to 20 carbon atoms, wherein the moiety is selected from the group consisting of alkyl, alkenyl, aryl, alkylaryl, arylalkyl, and alkylidene;

A', which are the same or different, are selected from the group consisting of methoxymethyl, t-butoxymethyl, tetrahydropyranyl, tetrahydrofuranyl, 1-ethoxyethyl, 1-methyl-1-methoxyethyl, and t-butyl; and a comprises an integer of from 4 to 8;

whereby one reactive bond between a silicon atom and an oxygen atom of the dehydroxylated silica support is cleaved, whereby one O-A' bond in the metallocene compound of Chemical Formula 7 is cleaved to yield a metallocene portion and A', and whereby two new bonds are formed, wherein the metallocene portion is bonded to the silicon atom of the dehydroxylated silica support via the oxygen atom previously bonded to A', and simultaneously A' is bonded to another silicon atom of the dehydroxlated silica support via the oxygen atom previously bonded to the silicon atom, to yield a supported metallocene catalyst of formula:

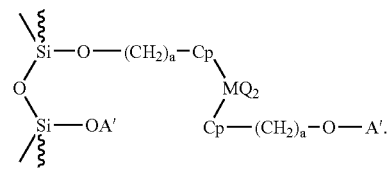

5. The method according to claim 4, wherein A' comprises t-butyl.

6. The method according to claim 4, wherein a is 6.

7. A supported metallocene compound prepared by the reaction of:

a) a metallocene compound of Chemical Formula 1 or Chemical Formula 2, wherein Chemical Formula 1 comprises:

$$(C_5R^1_m)_pD_s(C_5R^1_m)MQ_{3-p} \qquad 1$$

and wherein Chemical Formula 2 comprises:

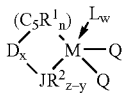

wherein at least one moiety selected from the group consisting of $R^1$, $R^2$, and D is substituted by a group of Chemical Formula 6, wherein:

M is a transition metal of Group 4;

$(C_5R^1{}_m)$ and $(C_5R^1{}_n)$ each comprise a cyclopentadienyl ring, wherein $R^1$, which are the same or different, are selected from the group consisting of hydrogen, $C_{1-40}$ alkyl, $C_{3-40}$ cycloalkyl, $C_{6-40}$ aryl, $C_{2-40}$ alkenyl, $C_{7-40}$ alkylaryl, $C_{7-40}$ arylalkyl, $C_{8-40}$ arylalkenyl, and a metalloid of Group 14 substituted by a hydrocarbyl group; or two $R^1$ form a hydrocarbyl group which joins together two adjacent carbon atoms of a cyclopentadienyl ring to form one or more $C_4$–$C_{16}$ rings;

D is selected from the group consisting of an alkylene carbon chain, an arylene carbon chain, an alkenylene carbon chain, a dialkyl germanium, a dialkyl silicon, an alkyl phosphine, an alkyl amine group substituting on and bridging two cyclopentadienyl ligands, and an alkyl amine group substituting on and bridging a cyclopentadienyl ligand and $JR^2{}_{z-y}$ ligand by covalent bonds;

$R^2$ is selected from the group consisting of hydrogen, $C_{1-40}$ alkyl, $C_{6-40}$ aryl, $C_{2-40}$ alkenyl, $C_{7-40}$ alkylaryl, and $C_{7-40}$ arylalkyl;

J comprises an element of Group 15 or Group 16;

Q, which are the same or different, are selected from the group consisting of halogen, $C_{1-20}$ alkyl, $C_{2-20}$ alkenyl, $C_{6-20}$ aryl, $C_{7-20}$ alkylaryl, and $C_{2-20}$ alkylidene;

L comprises a Lewis base;

s is 0 or 1 and p is 0, 1 or 2, provided that when p is 0 then s is 0, when s is 1 then m is 4 and p is 1, and when s is 0 then m is 5 and p is 0;

when J is an element of Group 15 then z is 3, and when J is an element of Group 16 then z is 2;

x is 0 or 1, provided that when x is 0 then n is 5, y is 1, and w is greater than 0, and when x is 1, then n is 4, y is 2, and w is 0; and wherein Chemical Formula 6 comprises:

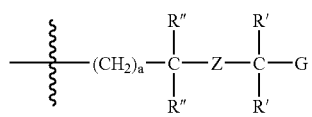

wherein Z is an oxygen atom or a sulfur atom;

R', which are the same or different, are selected from the group consisting of hydrogen, $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{1-20}$ arylalkenyl; or two R' are joined together to form a ring;

R", which are the same or different, are selected from the group consisting of hydrogen, $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{8-20}$ arylalkenyl;

G is selected from the group consisting of $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{8-20}$ arylalkenyl, $C_{1-20}$ alkoxy, $C_{6-20}$ aryloxy, $C_{1-20}$ alkylthio, $C_{6-20}$ arylthio, phenyl, and substituted phenyl; or G and R' join together to form a ring;

a is an integer of 4 to 8, provided that when Z is a sulfur atom then G is alkoxy or aryloxy; and when G is not an alkoxy or aryloxy then Z is an oxygen atom; and b) a dehydroxylated silica support of the following formula including a hydroxyl group amount of less than 0.5 mmol/g silica:

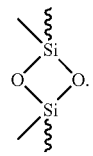

8. The supported metallocene compound according to claim 7, wherein G is selected from the group consisting of hydrogen, $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, $C_{8-20}$ arylalkenyl, phenyl, and substituted phenyl.

9. The supported metallocene compound according to claim 7, wherein —CR'$_2$G comprises t-butyl.

10. The supported metallocene compound according to claim 7, wherein a is 6.

11. A method for preparing a supported metallocene compound, the method comprising the step of:

reacting a metallocene compound of Chemical Formula 1 or Chemical Formula 2 with a dehydroxylated silica support including a hydroxyl group amount of less than 0.5 mmol/g silica in an organic solvent, wherein Chemical Formula 1 comprises:

$(C_5R^1{}_m)_pD_s(C_5R^1{}_m)MQ_{3-p}$ and wherein Chemical Formula 2 comprises:

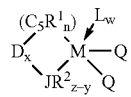

wherein at least one moiety selected from the group consisting of $R^1$, $R^2$, and D is substituted by a group of chemical Formula 6, wherein:

M is a transition metal of Group 4;

$(C_5R^1{}_m)$ and $(C_5R^1{}_n)$ each comprise a cyclopentadienyl ring, wherein $R^1$, which are the same or different, are selected from the group consisting of hydrogen, $C_{1-40}$ alkyl, $C_{3-40}$ cycloalkyl, $C_{6-40}$ aryl, $C_{2-40}$ alkenyl, $C_{7-40}$ alkylaryl, $C_{7-40}$ arylalkyl, $C_{8-40}$ arylalkenyl, and a metalloid of Group 14 substituted by a hydrocarbyl group; or two $R^1$ form a hydrocarbyl group which joins together two adjacent carbon atoms of a cyclopentadienyl ring to form one or more $C_4$–$C_{16}$ rings;

D is selected from the group consisting of an alkylene carbon chain, an arylene carbon chain, an alkenylene carbon chain, a dialkyl germanium, a dialkyl silicon, an alkyl phosphine, an alkyl amine group substituting on and bridging two cyclopentadienyl ligands, and an alkyl amine group substituting on and bridging a cyclopentadienyl ligand and $JR^2{}_{z-y}$ ligand by covalent bonds;

$R^2$ is selected from the group consisting of hydrogen, $C_{1-40}$ alkyl, $C_{6-40}$ aryl, $C_{2-40}$ alkenyl, $C_{7-40}$ alkylaryl, and $C_{7-40}$ arylalkyl;

J comprises an element of Group 15 or Group 16;

Q, which are the same or different, are selected from the group consisting of halogen, $C_{1-20}$ alkyl, $C_{2-20}$ alkenyl, $C_{6-20}$ aryl, $C_{7-20}$ alkylaryl, and $C_{2-20}$ alkylidene;

L comprises a Lewis base;

s is 0 or 1 and p is 0, 1 or 2, provided that when p is 0 then s is 0, when s is 1 then m is 4 and p is 1, and when s is 0 then m is 5 and p is 0;

when J is an element of Group 15 then z is 3, and when J is an element of Group 16 then z is 2;

x is 0 or 1, provided that when x is 0 then n is 5, y is 1, and w is greater than 0, and when x is 1, then n is 4, y is 2, and w is 0; and wherein the group of Chemical Formula 6 comprises:

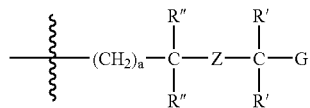

6 wherein Z is an oxygen atom or a sulfur atom;

R', which are the same or different, are selected from the group consisting of hydrogen, $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{8-20}$ arylalkenyl; or two R' join together to form a ring;

R", which are the same or different, are selected from the group consisting of hydrogen, $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{8-20}$ arylalkenyl;

G is selected from the group consisting of $C_{1-20}$ alkyl, $C_{3-20}$ cycloalkyl, $C_{6-20}$ aryl, $C_{2-20}$ alkenyl, $C_{7-20}$ alkylaryl, $C_{7-20}$ arylalkyl, and $C_{8-20}$ arylalkenyl, $C_{1-20}$ alkoxy, $C_{6-20}$ aryloxy, $C_{1-20}$ alkylthio, $C_{6-20}$ arylthio, phenyl, and substituted phenyl; or G and R' join together to form a ring;

a is an integer of 4 to 8, provided that when Z is a sulfur atom then G is alkoxy or aryloxy; and when G is not an alkoxy or aryloxy then Z is an oxygen atom; and wherein the dehydroxylated silica support is of formula:

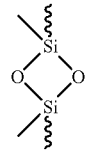

whereby a reactive bond between a silicon atom and an oxygen atom of the dehydroxylated silica support is cleaved, whereby a bond between an oxygen atom and a carbon, atom in Chemical Formula 6 of the metallocene compound is cleaved to yield a metallocene compound portion comprising the oxygen atom and a remaining portion comprising the carbon atom, and whereby the metallocene compound portion is bonded to the silicon atom of the dehydroxylated silica support, and simultaneously the remaining portion is bonded to the oxygen atom of the dehydroxylated silica support.

* * * * *